(12) United States Patent
Himmelhaus et al.

(10) Patent No.: US 8,502,972 B2
(45) Date of Patent: Aug. 6, 2013

(54) CLUSTERS OF MICRORESONATORS FOR CAVITY MODE OPTICAL SENSING

(75) Inventors: Michael Himmelhaus, Berlin (DE); Alexandre Francois, Chuo-ku (JP)

(73) Assignee: Fujirebio Inc., Tokyo (JP)

( * ) Notice: Subject to any disclaimer, the term of this patent is extended or adjusted under 35 U.S.C. 154(b) by 233 days.

(21) Appl. No.: 12/811,166

(22) PCT Filed: Dec. 25, 2008

(86) PCT No.: PCT/JP2008/073939
§ 371 (c)(1),
(2), (4) Date: Oct. 5, 2010

(87) PCT Pub. No.: WO2009/084721
PCT Pub. Date: Jul. 9, 2009

(65) Prior Publication Data
US 2011/0019186 A1 Jan. 27, 2011

Related U.S. Application Data

(60) Provisional application No. 61/018,144, filed on Dec. 31, 2007.

(51) Int. Cl.
*G01N 21/31* (2006.01)

(52) U.S. Cl.
USPC ........... 356/302; 356/300; 356/317; 356/436; 356/437; 436/165; 422/82.05

(58) Field of Classification Search
USPC ............... 356/300, 302, 436, 437; 422/82.05, 422/82.11; 435/6; 436/524; 385/12
See application file for complete search history.

(56) References Cited

U.S. PATENT DOCUMENTS

| | | | | |
|---|---|---|---|---|
| 6,490,039 | B2 * | 12/2002 | Maleki et al. | 356/436 |
| 7,123,359 | B2 * | 10/2006 | Armstrong et al. | 356/301 |
| 7,384,797 | B1 * | 6/2008 | Blair | 436/524 |
| 7,957,617 | B2 * | 6/2011 | Vollmer et al. | 385/39 |
| 8,124,927 | B2 * | 2/2012 | Savchenkov et al. | 250/227.24 |
| 2002/0068018 | A1 | 6/2002 | Pepper et al. | |
| 2004/0196465 | A1 | 10/2004 | Arnold et al. | |
| 2006/0123900 | A1 | 6/2006 | Sugita | |

(Continued)

FOREIGN PATENT DOCUMENTS

| | | | |
|---|---|---|---|
| JP | 2003-515737 A | 5/2003 | |
| JP | 2004-151093 A | 5/2004 | |

(Continued)

OTHER PUBLICATIONS

Supplementary European Search Report and Written Opinion corresponding to European Patent Application No. 08869004.5, dated Dec. 30, 2010.

(Continued)

*Primary Examiner* — Layla Lauchman
(74) *Attorney, Agent, or Firm* — Sughrue Mion, PLLC

(57) ABSTRACT

A method for sensing a target object using optical mode excitations in microresonators, comprises: preparing at least one cluster including at least two microresonators; obtaining some first spectra of the cluster; adsorbing the target object on a surface of the cluster; obtaining some second spectra of the cluster; and sensing the target object by comparing a lineshape of the first spectra with a lineshape of the second spectra.

20 Claims, 15 Drawing Sheets

(A)

(B)

U.S. PATENT DOCUMENTS

| | | |
|---|---|---|
| 2006/0274989 A1 | 12/2006 | Gergely et al. |
| 2007/0178607 A1 | 8/2007 | Prober et al. |
| 2010/0227315 A1* | 9/2010 | Poetter et al. .................. 435/6 |

FOREIGN PATENT DOCUMENTS

| | | |
|---|---|---|
| JP | 2004-515764 A | 5/2004 |
| WO | 01/40757 A2 | 6/2001 |
| WO | 2005/081707 A2 | 9/2005 |
| WO | 2005/116615 A1 | 12/2005 |
| WO | 2007129682 A1 | 11/2007 |

OTHER PUBLICATIONS

Gomez D. E. et al., Tunable Whispering Gallery Mode Emission From Quantum-Dot-Doped Microspheres, vol. 1, No. 2, pp. 238-241. XP002549921.

Japanese Office Action corresponding to Japanese Patent Application No. 2010-525546, Jan. 8, 2013.

* cited by examiner (A)

(B)

(A) Fabry-Perot Modes (FPM)    (B) Whispering Gallery Modes (WGM)

(A)     (B)

(A)

(B)

(A)

(B)

(A)

(B)

(A)  (B)

CLUSTERS OF MICRORESONATORS FOR CAVITY MODE OPTICAL SENSING

This application is a non-provisional application claiming a priority based on a prior U.S. Provisional Application No. 61/018,144 filed on Dec. 31, 2007. The entire contents of the Provisional Application No. 61/018,144 are incorporated by reference.

The entire contents of a prior PCT application No. PCT/EP2006/003714 which was filed on Apr. 21, 2006, a prior PCT application No. PCT/JP2007/059443 which was filed on Apr. 26, 2007, a prior U.S. provisional patent application No. 61/111,369 which was filed on Nov. 5, 2008, a prior U.S. provisional patent application No. 61/112,410 which was filed on November 7, a prior PCT application No. PCT/JP2008/05959 which was filed on May 19, 2008, and a prior PCT application No. PCT/JP2007/07534 which was filed on Dec. 21, 2007 are incorporated by reference.

TECHNICAL FIELD

The present invention relates to a technology for an optical biosensor based on optical cavity mode excitations in clusters of microresonators.

BACKGROUND ART

Optical microresonators confine light to small volumes by resonant recirculation and have demonstrated potential use as microscopic light emitters, lasers, and sensors (K. J. Vahala, Nature 424, pp. 839-846, 2003). The recirculation imposes geometry-dependent boundary conditions on wavelength and propagation direction of the light kept inside the microresonator. Accordingly, only certain optical modes, the so-called "cavity modes", can be efficiently excited. Since the energy levels of these allowed modes depend crucially on geometry and optical properties of the microresonators, the latter comprise very sensitive microscopic optical sensors that can be used for example to sense forces (e.g. by deformation of the cavity, cf., e.g., M. Gerlach et al., Opt. Express 15, 6, pp. 3597-3606, 2007) or changes in chemical concentration (e.g. by a corresponding change of the refractive index in close vicinity of the microresonator, cf., e.g., A. M. Armani, K. J. Vahala, Opt. Lett. Vol. 31, pp. 1896-1898, 2006). Similarly, microresonators can be used for biomolecular detection, e.g. by absorption of specifically binding molecules to or into a microresonator and detecting the resultant change of the refractive index around or inside of the cavity.

The confinement of light inside of a microresonator requires a highly reflective boundary between the microresonator and its surrounding. This can be achieved for example via total internal reflection (TIR), similarly to the guidance of light inside of an optical waveguide. As shown in FIG. 1A, TIR can occur if the refractive index of the microresonator, $n_{cav}$, is larger than that of its surrounding, $n_{env}$, i.e. $n_{cav} > n_{env}$. However, even in this case, TIR occurs only for angles α above a so-called "critical angle" $\alpha_{crit} = \arcsin(n_{env}/n_{cav})$, where α is measured from the local surface normal inside of the cavity, where the reflection occurs (FIG. 1A). Such simple considerations remain valid as long as surface roughness is negligible as compared to the wavelength of the light stored inside the microresonator. Accordingly, one general lower size limit of microresonators is given by the precision to which smooth surfaces can be prepared.

Another obstacle for utilization of microresonators is directly related to the requirement of a highly reflective interface between microresonator and surrounding. Since the path of light is reversible in absorption-free media, the interface will be also highly reflective for those light beams that impinge onto the interface from the surrounding. Accordingly, just those optical modes inside the cavity, which fulfill the requirement of high reflectivity and thus provide high light storage potential, cannot be easily populated by light accessing the microresonator from the outside.

Vollmer and coworkers (F. Vollmer et al., Applied Physics Letters 80, pp. 4057-4059, 2002) used evanescent field coupling between the uncoated core of an optical fiber and a silica microsphere for population of the cavity modes inside of the microsphere. In this case, photons can transit from the high refractive index core of the fiber to the high refractive index interior of the microsphere via tunneling. However, it has been demonstrated by Z. Guo et al. (Journal of Physics D: Applied Physics 39, pp. 5133-5136, 2006) that the coupling efficiency as well as the frequencies of the generated cavity modes within the cavity are highly depending on the distance between the optical fiber and the cavity. As a consequence, both the microsphere and the optical fiber have to be fixed to a solid mount in order to keep the distance between them constant. Vollmer et al. were able to demonstrate cavity mode biosensing via adsorption of Bovine Serum Albumin (BSA) onto the outer surface of silica spheres with diameters of 300 μm. They showed that the sensitivity of their sensor scales with 1/R, where R is the particle radius.

Kuwata-Gonokami and coworkers (M. Kuwata-Gonokami et al., Jp. J. Appl. Phys. Vol. 31, pp. L99-L101, 1992) used dye-doped polystyrene (PS) microspheres for populating cavity modes. The microspheres were radiated with ultrashort laser pulses to excite the dye molecules. The pump laser pulse was incident onto the microsphere surface at a small incidence angle α, so that the light could penetrate into the optically denser microsphere with small loss only (typically 5-10%). The excited dye molecules inside of the microresonator re-radiate fluorescent light into arbitrary directions, i.e. also into those which fulfill the condition of total internal reflection. Accordingly, all cavity modes, which fell into the emission wavelength range of the dye molecules, became excited. At high pump intensities lasing was observed.

Woggon and coworkers (M. V. Artemyev and U. Woggon, Applied Physics Letters 76, pp. 1353-1355, 2000; B. Möller et al., Applied Physics Letters 80, pp. 3253-3255, 2002) used semiconductor quantum dots for doping of polymer latex beads. Similar to the work of Kuwata-Gonokami and coworkers, the cavity modes inside of the latex beads can be populated by excitation of the semiconductor quantum dots with light of suitable wavelength. The quantum dots then re-emit fluorescent light that excites those cavity modes within their emission range. In general, the emission bandwidth of quantum dots amounts to some tens of nanometers, i.e. it is smaller than that of most dye molecules. One major advantage of quantum dots is, however, their much higher stability with respect to photobleaching. Recently, Woggon and coworkers used this scheme also for the excitation of cavity modes in coupled microresonators (B. M. Möller et al., Optics Letters 30, pp. 2116-2118, 2005).

Halas and coworkers have suggested core-shell particles of much smaller size consisting of a non-metallic core and a metallic shell for optical biosensing (West et al., U.S. Pat. No. 6,699,724 B1). They studied in particular the size regime from few tens to several hundreds of nanometers, i.e. particles with an outer diameter <1 μm. The conductive shell of such particles can be optically excited at the so-called "plasma frequency", which corresponds to a collective oscillation of the free electrons of the shell. While the plasma frequency of solid metal particles shows only marginal dependence on the particle size and is basically given by the physical properties of the bulk material, such as electron density and effective electron mass, Halas et al. were able to demonstrate that in the case of core-shell particles the position of the plasma frequency can be tuned over a wide range from the visible to the near infrared solely by changing the ratio between core and shell radii of the particles (N. Halas, Optics & Photonics News 13, 8, pp. 26-31, 2002; S. J. Oldenburg et al., Chemical Physics Letters 288, pp. 243-247, 1998). Halas et al. suggested to use such particles as biosensors by tuning the plasma frequency into a frequency range where it could support surface enhanced Raman emission of organic molecules adsorbed on the outer shell surface. The Raman emission then can serve as qualitative measure of protein adsorption. It must be noted, that Halas et al. used the core-shell character of the fabricated particles solely for tuning of the plasma frequency but not for generation or utilization of microresonator modes. In the course, they have not suggested to embed any kind of fluorescent material into the non-metallic particle cores for population of such modes.

A variety of cavity geometries has been studied so far. The most simple ones are microspheres, such as used by Vollmer et al. (F. Vollmer et al., Applied Physics Letters 80, pp. 4057-4059, 2002), rings or cylinders (D. K. Armani et al., Nature 421, pp. 925, 2003; H. J. Moon et al., Optics Communications 235, pp. 401, 2004). More complex cavities with lower degree of symmetry can also be used for the excitation of cavity modes, such as nanocrystals with hexagonal cross section (T. Nobis et al, Physical Review Letters 93, 10, 103903, 2004) or asymmetric cavities (Nöckel et al., Nature 385, pp. 45, 1997). Scherer and coworkers (O. Painter et al., Science 284, pp. 1819-1821, 1999) utilized photonic crystal structures and achieved the so far smallest microresonator volumes of 0.03 cubic micrometers with a single defect in a two-dimensional photonic crystal.

Several groups studied optical cavity mode spectra of assemblies of microresonators, such as dimers (T. Mukaiyama et al., Phys. Rev. Lett. Vol. 82, pp. 4623-4626, 1999), trimers and tetramers (B. M. Möller et al., Phys. Rev. B Vol. 70, pp. 115323/1-5, 2004), and linear chains (M. Bayer et al., Phys. Rev. Lett. Vol. 83, pp. 5374-5377, 1999; V. N. Astratov et al., Appl. Phys. Lett. Vol. 85, pp. 5508-5510, 2004; B. M. Möller et al., Opt. Lett. Vol. 30, pp. 2116-2118, 2005), solely in air and not for the purpose of optical sensing, but instead for cavity quantum electrodynamic studies and the development of coupled-resonator optical waveguides. In contrast to the present embodiment, most of these works utilized microresonators of same size and geometry (e.g. microstructured by means of lithographic patterning (Bayer et al.) or size-selected colloidal spheres (Mukaiyama et al., Möller et al.) with exactly matching cavity mode spectra to allow tight coupling and mode splitting, which is not observable otherwise (cf. e.g. Mukaiyama et al.). The utilization of microresonators of same geometry and size for the formation of assemblies of microresonators jeopardizes the idea of a characteristic spectral fingerprint for identification of a cluster of microresonators within an ensemble of clusters as implemented by the present embodiment. In fact, it is one of the key ideas of the present embodiment to take advantage of the size distribution of microresonators brought about by their fabrication and to utilize this variety for the generation of characteristic spectral fingerprint spectra. Further, Astratov and coworkers (V. N. Astratov et al., Appl. Phys. Lett. Vol. 85, pp. 5508-5510, 2004) studied optical coupling and transport phenomena in chains of spherical dielectric microresonators with a slight size dispersion of 1%. The chains consisted of a chain of non-fluorescent PS beads with one fluorescent bead at the top. The WGM emission of this bead was then traced down through the chain. As shown in FIG. 2 of that article, while the intensity drops from bead to bead with increasing distance from the light emitting bead for different modes to different extent, the observable WGM spectrum is always that of a single sphere, i.e. the non-fluorescing beads to not influence the WGM emission in terms of resonance positions or bandwidths. Effects of utilizing different chains on the appearance of the WGM spectrum of the light-emitting bead are not reported. Thus, conclusions about the existence of spectral fingerprint spectra in clusters of beads, in particular with larger size dispersion, cannot be drawn. More recently, Ashili et al. (S. P. Ashili et al., Opt. Express Vol. 14, pp. 9460-9466, 2006) studied optical coupling of cavity modes between two microspheres with large radius mismatch (8 and 5 µm diameters, respectively) as a function of their separation. While a slight blue shift of the WGM positions with decreasing gap size between the two microresonators was observed, this shift was attributed to a substrate effect and not to the sphere-sphere interaction. Therefore, no indication of the presence of spectral fingerprints is given. Summarizing, the studies found in the literature on optical cavity mode spectra of assemblies of microresonators do not give any evidence for the existence of spectral fingerprints as implemented in the present embodiment nor do they discuss the application of assemblies or clusters of microresonators for optical sensing applications.

For biosensing applications by means of optical cavity mode tracking in microresonators, so far mainly non-metallic microresonators have been applied. Ilchenko & Maleki (Proceedings SPIE, 4270, pp. 120-130, 2001) have described a set-up for using whispering gallery mode resonators with very high quality factors as optical sensors by monitoring the decrease of the quality factor due to molecular adsorption on the resonator surface. This principle requires very high quality factors in the range $Q \sim 10^8 - 10^9$, which are achievable only in resonators of several tens to several hundreds micrometers in diameter. Smaller resonators have typically much higher losses, and accordingly, lower quality factors. Therefore, the approach suggested here is not well suited for the development of an optical sensor with a total size of less than few tens of micrometers.

Maleki et al. (U.S. Pat. No. 6,490,039 B2) have described how to use a single microparticle with a spherical shape for biosensing. The detection is based on the cavity mode wavelength shift that occurs when a (bio-)molecule is adsorbed on the microsphere surface. The experimental setup requires a single microparticle with a high quality factor, which will host the cavity modes and act as a transducer. The cavity modes are generated by TIR within the microparticle using an incoming laser coupled to the microparticle by an optical fiber. The output signal is also collected by an optical fiber and then analyzed. The wavelength shift of the cavity modes provides information whether the (bio-) molecule is attached to the microparticle or not.

Poetter et al. (PCT/AU2005/000748, 2005) have applied a similar approach for biosensing by means of cavity modes. Following the approach of Woggon and coworkers, they have used fluorescent microparticles or particles that contain quantum dots. In that case, the cavity modes are excited by emission of the fluorophore inside of the sphere so that coupling between the microsphere and an optical fiber is not required. This approach further enables the use of different types of light sources (UV lamp, HeNe gas laser, Argon ion laser, HeCd gas laser, etc.) for the excitation of the fluorophore and thus the cavity modes.

Noto et al. (Applied Physics Letters 87, pp. 223901-1 223901-3, 2005; Biophysical Journal 92, pp. 4466-4472, 2007) have shown that biosensors based on cavity modes can be used not only in order to detect the presence of biomolecules attached on the surface of a microsphere but also in order to get some relevant information about the biomolecule itself. The authors have shown that the wavelength shift depends on the molecular weight of the biomolecule considered. The authors also pointed out that it is possible to determine the orientation of the biomolecule attached to the microsphere by comparing the cavity mode wavelength shift of different kinds of cavity mode excitations (transverse electric (TE) and transverse magnetic (TM) modes). The latter experiments have been performed with Bovine Serum Albumin (BSA) adsorbed onto the surface of a silica sphere (r=200 μm).

Vollmer et al. (Biophysical Journal 85, pp. 1974-1979, 2003), have described a biosensor for the detection of DNA based on the detection of cavity modes in single silica microspheres. The authors used two single microspheres (r=200 μm) that were functionalized with oligonucleotides in order to interact specifically with different nucleic acids. They demonstrated the multiplexed detection of specific DNA sequences by applying two microspheres coupled to a common optical fiber. In contrast to the present embodiment, the microspheres were operated independently of each other to assure an independent sensor signal. While the WGM resonance positions were detected through the same fiber, they were independently traced. In particular, no cross-coupling between the two microspheres, which were placed several micrometers apart from each other, was observed (p. 1976, $1^{st}$ column, $3^{rd}$ line from bottom). Further, the authors did not report about any specific differences in the spectra obtained from different sets of microspheres, i.e. they did not report about the existence of spectral fingerprints as defined in the present embodiment.

Teraoka et al. (Journal of Optical Society of America B 23, 7, pp. 1434-1441, 2006) have more recently described how to improve the sensitivity of biosensors based on cavity modes. The authors have coated a silica microsphere with a layer of higher refractive index material, in that case polystyrene. The authors have claimed a significant improvement in sensitivity towards biomolecular detection with this coated microsphere.

A number of groups have applied non-metallic optical microresonators as sensors in liquid environment, for example for remote refractive index sensing (P. Zijlstra et al., Appl. Phys. Lett. Vol. 90, pp. 161101/1-3, 2007; S. Pang et al. Appl. Phys. Lett. Vol. 92, pp. 221108/1-3, 2008; J. Lutti et al., Appl. Phys. Lett. 93, 15113/1-3, 2008). None of these groups however, have considered or investigated the optical properties and/or the application of clusters of microresonators.

Other groups have achieved lasing in microcavities, i.e. the fabrication and utilization of microlasers (e.g. M. Kuwata-Gonkami & K. Takeda, Opt. Mater. Vol 9, pp. 12-17, 1998; V. Sandoghar et al. Phys. Rev. A Vol. 54, pp. R1777-R1780, 1996; S. M. Spillane et al., Nature Vol. 415, pp. 621-623, 2002; Z. Zhang et al., Appl. Phys. Lett. 90, 111119/1-3, 2007). The achievement of lasing in clusters of microresonators, in particular in liquid environment and/or for biosensing application, however, has not been reported so far.

Summarizing, the work utilizing non-metallic microresonators for sensing applications has so far only been performed by utilization of isolated microresonators. In the case that multiplexing is discussed, i.e. the application of more than a single microresonator for parallel detection of a variety of analytes, the different microresonators applied are thought to be operated independently of each other.

The application of optical cavity modes of metal-coated dielectric particles to biosensing is described in WO2007129682. There, also clusters of metal-coated dielectric particles are described. However, there is no mention throughout the text that cavity mode spectra obtained from clusters of resonators may exhibit a characteristic fingerprint, which may be used for their recognition and/or an facilitated readout process.

Besides closed microresonators, also the utilization of open microresonators has been suggested for biosensing. These microresonators comprise microscopic vacancies in a thin metallic film. The light is confined only in the plane of the thin film, but free in perpendicular direction. Blair and coworkers (Y. Liu et al., Nanotechnology, 15, pp. 1368-1374, 2004; Y. Liu & S. Blair, Proceedings of SPIE, 5703, pp. 99-106, 2005) studied fluorescent enhancement of dye-labeled proteins adsorbed inside of nanocavities patterned in a thin gold film. They observed fluorescent enhancement by a factor of 2 and an increase in quantum yield by a factor of 6. While the authors have utilized assemblies of nanofabricated cavities basically to increase signal intensity, they have not spectrally analyzed the fluorescence emission obtained from their samples. Therefore, they were not able to observe neither optical cavity modes in general nor any characteristic spectral fingerprints as notably described in the present embodiment. In addition, the existence of such characteristic fingerprints is very unlikely in their case for two reasons. Firstly, the method relies on regular patterns, secondly, it applies electron beam lithography for their fabrication. Due to the excellent precision of this technique, deviations from the regularity of the pattern are expectedly small, thus jeopardizing the occurrence of spectral fingerprints, which are based on local deviations from the basic (regular) pattern.

There exist a variety of other methods for label-free biosensing based on plasma excitations of metal particles or thin metal films. In these cases, an incoming light wave is used to launch a freely propagating or localized surface plasmon (which corresponds to a collective oscillation of the free electrons of the metal). The plasmon in turn produces an evanescent electromagnetic wave in the close environment of the metal film or metal particle. When the dielectric properties in this environment are altered, e.g. due to biomolecular adsorption, the plasmon resonance position is changed. Accordingly, this shift can be used as read-out signal of a label-free optical biosensor. Examples of approaches utilizing localized plasmon effects are given in US 2003/0174384 A1, EP 0 965 835 A2, WO2006111414, Sensors and Actuators B Vol. 63, pp. 24-30, 2000, and Biosensors & Bioelectronics Vol. 22, pp. 3174-3181, 2007. WO2006111414 mentions explicitly the use of metal-coated clusters of fluorescent dielectric particles for biosensing. However, the use and/or excitation of optical cavity modes is neither discussed nor even mentioned.

An example for utilization of free-travelling plasmons is given by the Biacore system from General Electric Health Care, UK.

Recently, some groups discussed coupling between optical cavity modes and surface plasmons in single metal-coated particles (D. Amarie et al., Journal of Physical Chemistry B, Vol. 109, pp. 15515-15519, 2005) or in regular arrays of particles embedded in a metallic matrix (R. M. Cole et al., Physical Review Letters, Vol. 97, pp. 137401/1-4, 2006). The latter group did not report about characteristic spectral fingerprints, since they worked with periodic arrays of particles and could neglect the presence of imperfections. Further, their approach is not well suited for optical sensing, because surface plasmons are generated at the particle/metal interface, which is not easily accessible from the outside.

DISCLOSURE OF INVENTION

Technical Problem

The present invention has been achieved in order to solve the problems which may occur in the related arts mentioned above.

Technical Solution

The biosensor that has been invented relies on wavelength shifts of optical cavity modes as transducer mechanism for the detection of (bio-)molecules. It is composed of multiple microresonators, or clusters, that are positioned in close vicinity to each other or in contact, instead of a single isolated microresonator.

According to one aspect of the invention, a method for sensing a target object using optical mode excitations in microresonators, comprise: preparing at least one cluster including at least two microresonators; obtaining some first spectra of the cluster; adsorbing the target object on a surface of the cluster; obtaining some second spectra of the cluster: and sensing the target object by comparing a lineshape of the first spectra with a lineshape of the second spectra.

BRIEF DESCRIPTION OF DRAWINGS

FIG. 1 is a schematic view that depicts examples for potential reflective properties of cavity surfaces, wherein FIG. 1A shows the example in the case of a simple non-coated dielectric cavity in which light can be trapped via total internal reflection (TIR) for all incidence angles $\alpha_i$ above a so-called "critical angle", $\alpha_{crit}$, if the real part of the refractive index $n_{cav}$ of the cavity is larger than that of its environment $n_{cav}$ (light impinging onto the surface at an angle $\alpha_i < \alpha_{crit}$ can easily transmit through the surface, thereby also allowing access of the cavity from the outside, as needed, e.g. for optical pumping of fluorescent material inside of the cavity), and wherein FIG. 1B shows the example in the case of a coated cavity (with a high reflectivity at the wavelength of interest) in which light impinging onto the coating is reflected for arbitrary angles (this facilitates trapping of light inside of the cavity, but complicates optical access of the cavity from the outside, e.g. as needed for optical pumping of fluorescent material inside of the cavity);

FIG. 2 is a schematic view that depicts a simplifying estimation for characteristic cavity modes of spherical microresonators, wherein FIG. 2A shows the example of Fabry Perot Modes (FPM), and wherein FIG. 2B shows Whispering Gallery Modes (WGM);

FIG. 3 is a schematic view that depicts the wavelength shift of WGM induced by adsorption of a (bio-)molecule on a microsphere surface, wherein FIG. 3A shows the microsphere surface, and wherein FIG. 3B shows the wavelength shift of WGM;

FIG. 4 is a schematic view that depicts examples for cluster formation by individual microresonators on a substrate, optionally coated with shells, wherein FIG. 4A shows two microresonators without shell forming a cluster, wherein FIG. 4B shows five microresonators without shell forming a three-dimensional cluster, wherein FIG. 4C shows two microresonators coated individually with shells forming a cluster, wherein FIG. 4D shows two microresonators coated with a shell as a whole, which isolates their cores from the substrate, wherein FIG. 4E shows two microresonators coated individually with shells, which allow a direct contact of the cores with the substrate, but not to each other, wherein FIG. 4F shows two microresonators coated with a shell as a whole forming a cluster, which allows direct contact of the cores to each other as well as to the substrate, wherein FIG. 4G shows five microresonators coated individually with shells forming a three-dimensional cluster, and wherein FIG. 4H shows five microresonators coated with a shell as a whole forming a cluster, which allows direct contact of the cores to each other as well as to the substrate (these schemes can be easily extended to any other number of particles; also combinations of the schemes are possible);

FIG. 6 shows WGM spectra of a single microsphere (r=5 μm), wherein FIG. 6A shows the WGM spectrum measured in a dry environment, wherein FIG. 6B shows the WGM spectrum measured in water (both spectra have been measured from the same microparticle);

FIG. 7 shows a WGM spectrum of a single fluorescent polystyrene bead of 10 μm nominal diameter as well as WGM spectra of clusters containing a different number of such particles in Millipore water, wherein FIG. 7A shows a WGM spectrum of the single bead in water, wherein FIG. 7B shows a WGM spectrum of a cluster of 2 beads in water, wherein FIG. 7C shows a WGM spectrum of a cluster of 3 beads in water, and wherein FIG. 7D shows a WGM spectrum of a cluster of 4 beads in water;

FIG. 12 shows WGM spectra of a single microsphere (r=5 μm) after subsequent deposition of layers of polyelectrolyte (PE), wherein FIG. 12A shows WGM survey spectra, and wherein FIG. 12B shows a close-up as indicated by the black frame in FIG. 12A visualizing the wavelength shift of the WGM in more detail; spectra vertically displaced for clarity;

FIG. 13 shows WGM spectra of a cluster of 3 microspheres (r=5 μm) after subsequent deposition of layers of PE, wherein FIG. 13A shows WGM survey spectra, and wherein FIG. 13B shows a close-up as indicated by the black frame in FIG. 13A visualizing the wavelength shift of the WGM in more detail; spectra vertically displaced for clarity;

FIG. 14 displays the results of an autocorrelation calculated from WGM spectra of microsphere(s) prior to the adsorption of PE and after the $3^{rd}$ PE coating, respectively, wherein FIG. 14A shows the autocorrelation of a single microsphere, and wherein FIG. 14B shows the autocorrelation of a cluster of 3 microspheres; the insets show a close-up of the respective correlation maximum;

FIG. 15 displays the results of correlations calculated from WGM spectra of different microspheres, wherein FIG. 15A shows the correlation of two different single microspheres, wherein FIG. 15B shows the correlation of two different clusters containing each 3 microspheres; the insets show a close-up of the respective correlation maximum;

FIG. 17 shows the results of WGM measurements of the adsorption of BSA onto clusters and single microspheres, respectively, wherein FIG. 17A shows the wavelength shift of the WGM as a function of the number of microspheres constituting the cluster, and wherein FIG. 17B shows the results of the projected area of BSA as a function of the number of microspheres constituting the cluster as calculated from the WGM shifts shown in FIG. 17A; the error bars indicate the resolution of the detection unit (~0.01 nm); the experimental errors (measurements on different clusters with same number of beads) were found to be within these limits;

FIG. 18 is a schematic view that depicts examples for possible configurations of clusters of microresonators deposited on a substrate, wherein FIG. 18A shows random configurations, and wherein FIG. 18B shows ordered configurations;

BEST MODE FOR CARRYING OUT THE INVENTION

Exemplary embodiments relating to the present invention will be explained in detail below with reference to the accompanying drawings.

DEFINITION OF TERMS

BSA: Bovine serum albumin.
C6G: Coumarin 6 laser grade.
cw: Continuous wave.
DFB laser: Distributed feedback laser diode.
PAA: Poly(acrylic acid).
PAH: Poly (allylamine hydrochloride).
PBS: Phosphate buffered saline.
PE: Polyelectrolyte.
PS: Polystyrene.
PSS: Poly(sodium 4-styrenesulfonate).
TIR: Total internal reeflection.
TE: Transverse electric optical mode.
TM: Transverse magnetic optical mode.

Reflection and transmission at a surface: In general, the surface of a material has the ability to reflect a fraction of impinging light back into its ambient, while another fraction is transmitted into the material, where it may be absorbed in the course of its travel. In the following we call the power ratio of reflected light to incident light the "Reflectivity" or "Reflectance", R, of the ambient/material interface (or material/ambient interface). Accordingly, the power ratio of transmitted light to incident light is called the "Transmittance", T, of this interface. Note, that R and T both are properties of the interface, i.e. their values depend on the optical properties of both, the material and its ambient. Further, they depend on the angle of incidence and the polarization of the light impinging onto this interface. Both R and T can be calculated by means of the Fresnel equations for reflection and transmission.

Figure 1:
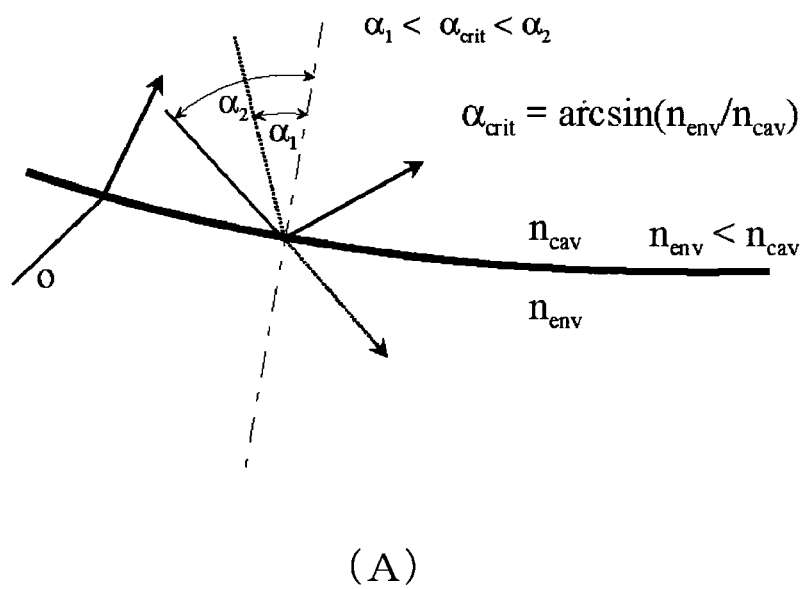
Figure 1:
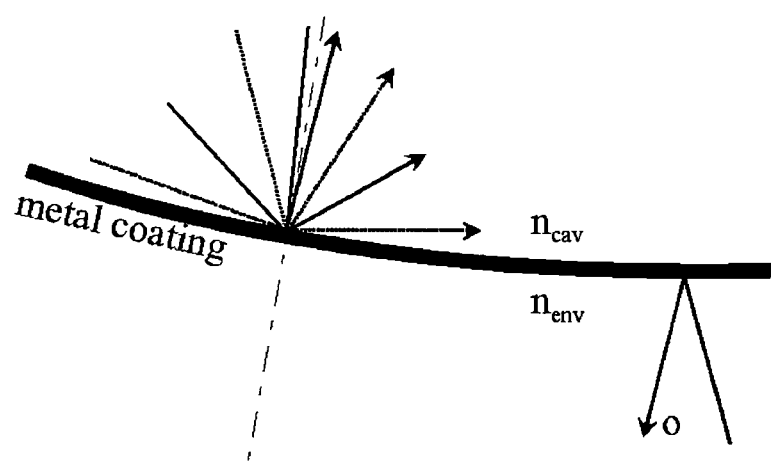

Optical cavity: An optical cavity is a closed volume confined by a closed boundary area (the "surface" of the cavity), which is—at least in some area and under suited conditions—highly reflective to light in the ultraviolet (UV), visible (vis) and/or infrared (IR) region of the electromagnetic spectrum. Besides its wavelength dependence, the reflectance of this boundary area may also be dependent on the incidence angle of the light impinging on the boundary area with respect to the local surface normal (cf. FIG. 1A). Further, the reflectance may depend on the location, i.e. where the light impinges onto the boundary area. The inner volume of the optical cavity may consist of vacuum, air, or any material that shows high transmission in the UV, visible, and/or IR. In particular, transmission should be high at least for a part of those regions of the electromagnetic spectrum, for which the surface of the cavity shows high reflectance. An optical cavity may be coated with a material different from the material of which the optical cavity is made. The material used for coating may have, e.g., different optical properties, such as different refractive index or absorption coefficient. Further it may comprise different physical, chemical, or biochemical properties than the material of the optical cavity, such as different mechanical, optical, electrical and/or magnetic properties, chemical inertness or reactivity, and/or antifouling or other biofunctional functionality. In the following, this optional coating is referred to as "shell", while the optical cavity is called "core". Further, the total system, i.e. core and shell together, are referred to as "(optical) microresonator". The latter term is also used to describe the total system in the case that no shell material is applied. Further, the term "cluster of microresonators" is used for an aggregate of microresonators, which are individually coated (e.g. bearing different kinds of shells), as well as for an aggregate of optical cavities, which are homogeneously or heterogeneously coated as a whole (e.g. after formation of the aggregate). In addition to the shell discussed here, a part of the surface of the microresonator or cluster of microresonators may be coated with additional layers (e.g. on top of the shell) as part of the sensing process, for example to provide a suitable (bio-)functional interface for detection, e.g. of specific binding events, or in the course of the sensing process when target molecules adsorb on the resonator surface or a part of it.

An optical cavity (microresonator) is characterized by two parameters: First, its volume V, and second, its quality factor Q. In the following, the term "optical cavity" ("microresonator") refers to those optical cavities (microresonators) with a quality factor Q>1. Depending on the shell material used, the light stored in the microresonator may be stored in the optical cavity solely, e.g. when using a highly reflective metal shell, or it may also penetrate into the shell, e.g. when using a dielectric or semiconducting shell. Therefore, it depends on the particular system under consideration, which terms (volume and Q-factor of the optical cavity or those of the microresonator) are more suitable to characterize the resulting optical properties of the microresonator. The definitions made below to characterize optical cavities (quality factor, volume of an optical cavity, optical cavity mode, mode coupling, optical contact, cluster, lasing threshold) therefore hold correspondingly for microresonators.

Quality factor: The quality factor (or "Q-factor") of an optical cavity is a measure of its potential to trap photons inside of the cavity. It is defined as $$Q = \frac{\text{stored energy}}{\text{loss per roundtrip}} = \frac{\omega_m}{\Delta\omega_m} = \frac{\lambda_m}{\Delta\lambda_m} \quad (1)$$

where $\omega_m$ and $\lambda_m$ are frequency and wavelength of cavity mode m, respectively, and $\Delta\omega_m$ and $\Delta\lambda_m$ are the corresponding bandwidths. The latter two equations connect the Q-factor with position and bandwidth of the optical modes inside of the cavity. Obviously, the storage potential of a cavity depends on the reflectance of its surface. Accordingly, the Q-factor may depend on the characteristics of the cavity modes, such as their wavelength, polarization, and direction of propagation.

Volume of an optical cavity: The volume of an optical cavity is defined as its inner geometrical volume, which is confined by the surface of the cavity, i.e. the reflective boundary area.

Optical cavity mode: An optical cavity mode or just "cavity mode" is a wave solution of the electromagnetic field equations (Maxwell equations) for a given cavity. These modes are discrete and can be numbered with an integer m due to the restrictive boundary conditions at the cavity surface. Accordingly, the electromagnetic spectrum in presence of the cavity can be divided into allowed and forbidden zones. The complete solution of the Maxwell equations consists of internal and external electromagnetic fields inside and outside of the cavity, respectively. In the following, the term "cavity mode" refers to the inner electromagnetic fields inside the cavity unless otherwise stated. The wave solutions depend on the shape and volume of the cavity as well as on the reflectance of the boundary area, i.e. the cavity surface.

Figure 2:
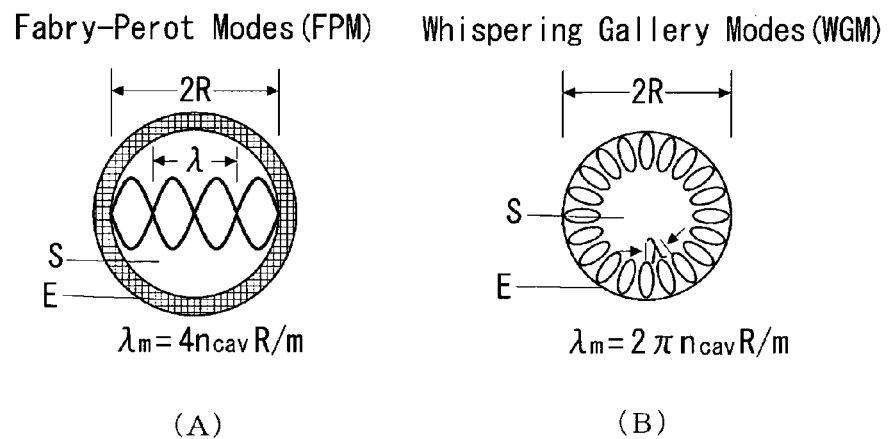

For spherical cavities, there exist two main types of solutions, for which the wavelength dependence can be easily estimated. For simplicity, we will use these estimates in the discussion below. FIG. 2 illustrates the difference between the two. We assume that in both cases a standing wave has formed. In FIG. 2A the standing wave formed in radial direction, while in FIG. 2B it formed along the circumference of the inner boundary between sphere and environment (in the case of a sphere coated with a metallic shell, the standing wave forms along the inner shell boundary). These standing waves can be viewed at as superpositions of counterpropagating traveling modes in either radial or azimuthal direction, respectively. In the following, we will call the modes in radial direction "Fabry-Perot Modes" (FPM) due to analogy with Fabry-Perot interferometers. The modes forming along the circumference of the spheres are called "Whispering Gallery Modes" (WGM) in analogy to an acoustic phenomenon discovered by Lord Rayleigh. For a simple mathematical description of the wavelength dependence of these modes, we use the standing wave boundary conditions in the following (for illustration, cf. FIG. 2):

$$\lambda_m = \frac{4Rn_{cav}}{m}, \quad m = 1, 2, 3, \ldots \quad (2)$$

for FPM, which states that the electric field at the inner cavity surface as to vanish for all times, as is the case e.g. for a cavity with a metallic coating. For WGM, the boundary conditions yield $$\lambda_m = \frac{2\pi R n_{cav}}{m}, \quad (3)$$

which basically states that the wave has to return in phase after a full roundtrip. In both formulas, "m" is an integer and is also used for numbering of the modes, R is the sphere radius, and $n_{cav}$ the refractive index inside of the cavity.

Mode coupling: We define mode coupling as the interaction between cavity modes emitted by two or more optical cavities or microresonators that are positioned in (physical) contact with each other or in close vicinity to allow an optical contact. As shown by Kuwata-Gonokami and coworkers, mode splitting due to tight coupling between microresonators may occur when microresonators of same geometry and size are brought into contact (T. Mukaiyama et al., Phys. Rev. Lett. Vol. 82, pp. 4623-4626, 1999). This phenomenon may also be utilized for fabrication of light-guiding structures (B. M. Möller et al., Opt. Lett. Vol. 30, pp. 2116-2118, 2005). In addition, as has been pointed out by Astratov and coworkers for microspheres with small (Appl. Phys. Lett. Vol. 83, pp. 5508-5510, 2004) and large size mismatch (S. P. Ashili et al., Opt. Express Vol. 14, pp. 9460-9466, 2006), light may also pass from one microresonator to a neighboring one if the size of the microresonators is in clear disparity. While this phenomenon is not related to tight coupling of optical cavity modes, it might also influence the lineshape of WGM spectra and therefore is included into the definition given here.

Optical contact: Two optical cavities or microresonators are said to have an "optical contact", if light can transmit from one cavity or resonator to the other one and vice versa. In this sense, an optical contact allows potentially for mode coupling between two resonators in the sense defined above. Accordingly, an optical cavity or microresonator has an optical contact with the substrate if it may exchange light with it.

Spectral fingerprint: A spectral fingerprint is defined as an optical cavity mode spectrum with a characteristic lineshape in the sense that different clusters of microresonators and/or optical cavities within in a set of clusters of interest (e.g. within the same sample, substrate or experiment) may be recognized and/or distinguished from each other by comparing their optical cavity mode spectra. In this sense a spectral fingerprint can be considered as an optical cavity mode spectrum, which is unique, e.g. in terms of mode positions, mode intensities, mode bandwidths and/or overall lineshape, within the set of optical cavity mode spectra of relevance, e.g. those that need to be compared with each other for identification of a wanted cluster of microresonators and/or optical cavities. It should be noted that whether a given set of microresonators and/or optical cavities exhibits a spectral fingerprint or not may depend on the way of its excitation and/or detection. In this sense, excitation and detection need to be performed in a suitable way. Further, the comparison of spectra may require a proper tool, such as a mathematical algorithm suitable for working out the differences in the different optical cavity mode spectra. Such mathematical tool, may be, for example, the calculation of correlation functions of different (or same) spectra as exemplified in Example 1.

Cluster: A cluster is defined as an aggregate of microresonators and/or optical cavities of arbitrary and optionally different geometry and shape, which may be formed either in a one-, two-, or three-dimensional fashion (cf. FIG. 4). The individual microresonators and/or optical cavities are either positioned in such a way that neighboring microresonators and/or optical cavities are in contact with each other or in close vicinity in order to promote the superposition of their optical cavity mode spectra and/or cavity mode coupling. Microresonators and/or optical cavities in contact may be in physical contact, i.e. touching each other, or, e.g., in optical contact as defined above. Microresonators and/or optical cavities in close vicinity to each other may be sufficiently close for superposition of their evanescent fields, which extent typically some hundreds of nanometers from their surface into the ambient, or sufficiently close for collective excitation and/or detection of their cavity mode spectra (independent of the timing of such collective excitation and/or detection). In the case that the microresonators and/or optical cavities are coupled to an optical fiber or waveguide or another kind of optical coupling device for their operation, e.g. excitation and/or detection, their arrangement with respect to each other (e.g. in terms of geometry and separation) is less important as long as spectra obtained from different systems yield distinguishable spectra, i.e. exhibit a spectral fingerprint. Then, the system "microresonators and/or optical cavities attached to the coupling device" that exhibits such spectral fingerprint may be considered as the "cluster of microresonators".

Alternatively, a cluster of microresonators and/or optical cavities is an aggregate of arbitrary geometry and shape of microresonators and/or optical cavities of arbitrary and optionally different geometry and shape, which is collectively operated, e.g. in which optical cavity modes are collectively excited and/or collectively detected. However, the term "collectively" is meant to be independent of the timing of excitation and/or detection, which may be performed in a parallel fashion (e.g. by simultaneous exposure of the entire cluster(s) to the excitation radiation and/or detection of the optical cavity mode spectra by means of an in parallel operating (multichannel) detection device, such as a detector array or a CCD camera) or in a serial way by scanning either the light source(s) and/or detector(s) through the wanted spectral range. Also, combinations of these parallel and serial schemes as well as more complex timing sequences are feasible. In this sense, a cluster of microresonators and/or optical cavities can also be viewed at as an aggregate of arbitrary geometry and shape of microresonators and/or optical cavities of arbitrary and optionally different geometry and shape, which exhibits a characteristic spectral fingerprint when probed under suitable conditions (independent of the timing and/or other relevant conditions). It should be further noted that the microresonators and/or optical cavities comprising the cluster may have different optical, physical, chemical and/or biological function and also bear different kinds of shells of different function. For example, they may exhibit different kinds of optical cavity mode spectra (e.g. FPM or WGM), which may be excited by different optical mechanisms (e.g., via evanescent field coupling or by excitation of one or different kinds of fluorescent material(s)). As already stated above, independent of its composition, the only crucial criterion is that the cluster exhibits a characteristic spectral fingerprint when probed and analyzed under suitable conditions.

Figure 4:
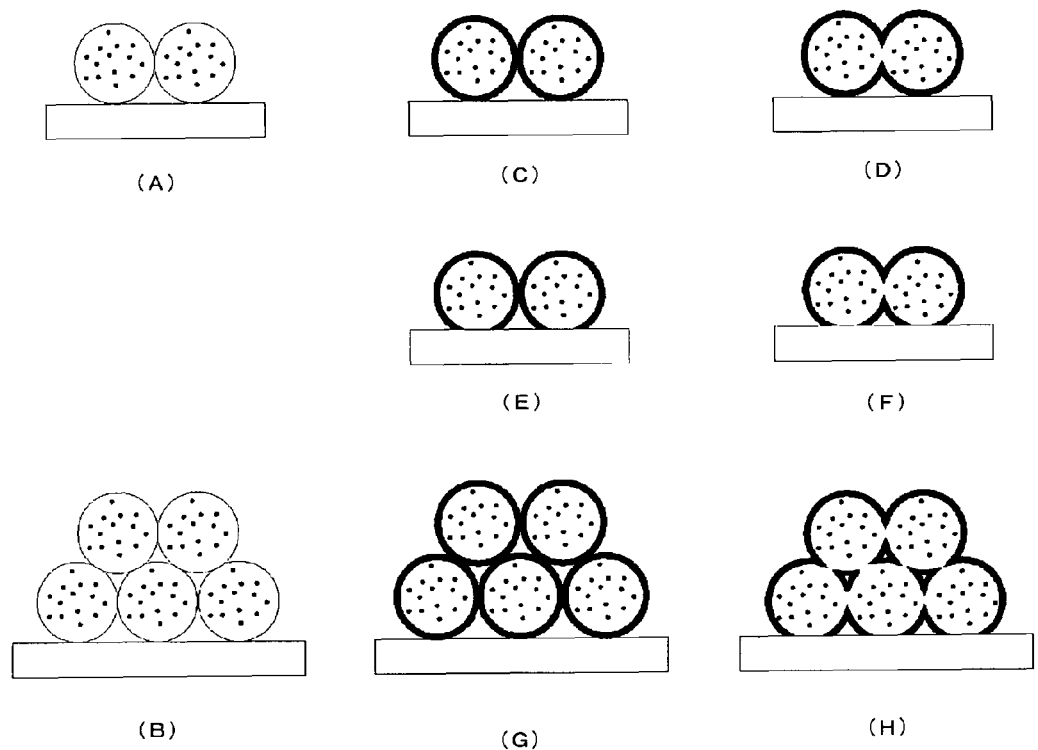
Figure 18:
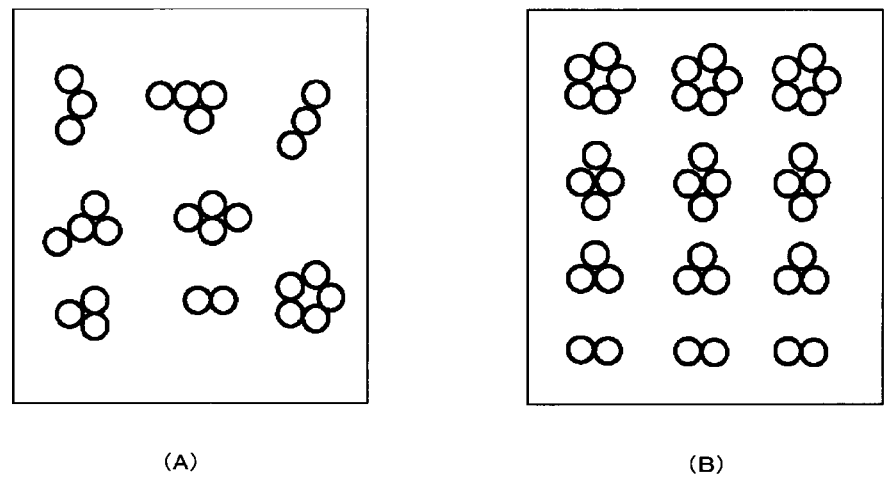

The microresonators and/or optical cavities (or the resulting clusters) may be attached to a surface (e.g. as illustrated in FIG. 4), embedded into a material, which is e.g. porous for an analyte, or move freely, e.g. float in a fluid medium. Further, the clusters or their constituent microresonators may be—at least temporally—detached from a surface, e.g. to float freely in a fluid medium or to penetrate a material for its analysis (e.g. a polymer, biopolymer, vesicle, liposome, cell membrane, live cell and/or tissue). The individual cavities may be coated as described above in either such a way that each cavity is individually coated (FIGS. 4C, 4E, 4G) or in such a way that the cavities (cores) are coated as a whole (FIGS. 4D, 4F, 4H). The shell may isolate the cores of the microresonators from each other (FIGS. 4C, 4E, 4G) and/or from the substrate (FIGS. 4C, 4D, 4G) or allow direct contact (FIGS. 4D, 4E, 4F, 4H). Further, combinations of the schemes shown in FIG. 4 are feasible. In general, the clusters of microresonators and/or optical cavities can be distributed over the surface in a random or an ordered fashion, thereby forming one-, two- or three-dimensional structures (FIGS. 4, 18). In that way, also photonic crystals may be formed. The clusters may be formed randomly or in an ordered fashion for example using micromanipulation techniques and/or micropatterning and/or self-assembly. Further, the clusters may form in suspension without supporting substrate. In such case and analogously to the description above, the cores of the individual microresonators comprising the cluster may be isolated by their shells from each other or in direct contact. Also, the clusters may form in the course of a sensing process, for example inside of a medium, such as a live cell, after penetration of at least a part of the microresonators forming the cluster(s) into the medium, to facilitate sensing of the wanted physical, chemical, biochemical, and/or biomechanical properties.

Lasing threshold: The threshold for stimulated emission of a microresonator (optical cavity), also called the "lasing threshold", is defined as the optical pump power of the microresonator where the light amplification via stimulated emission just compensates the losses occurring during propagation of the corresponding light ray within the microresonator. Since the losses for light rays traveling within a cavity mode are lower than for light rays that do not match a cavity mode, the cavity modes exhibit typically the lowest lasing thresholds (which may still differ from each other depending on the actual losses of the respective modes) of all potential optical excitations of a microresonator. In practice, the lasing threshold can be determined by monitoring the optical output power of the microresonator (e.g. for a specific optical cavity mode) as a function of the optical pump power used to stimulate the fluorescent material of the microresonator (also called the "active medium" in laser physics). Typically, the slope of this dependence is (significantly) higher above than below the lasing threshold so that the lasing threshold can be determined from the intersection of these two dependencies. When talking about the "lasing threshold of an optical microresonator", one typically refers to the lasing threshold of that optical cavity mode with the lowest threshold within the observed spectral range. Analogously, the lasing threshold of a cluster of microresonators addresses the lasing threshold of that optical cavity mode within the cluster with the lowest threshold under the given conditions.

The present invention provides a method for optical sensing using optical cavity mode excitations in clusters of microresonators. For sake of simplicity, the invention will be described using whispering gallery modes (WGM) emitted by dye-doped dielectric microspheres in a sensing application as an example. However, in principle, any other type of cavity mode excitation, for example the Fabry-Perot modes described above, with any kind of cavity geometry, material, shell, and/or coating, and applying any suitable method for cavity mode excitation and/or read-out may be utilized for the same or other purpose.

WGM have found applications in many areas of optics and photonics, e.g. due to their lasing properties (Wu et al., Physical Review A 60, 1, pp. 630-632, 1999 and Spillane et al., Nature 415, pp. 621-623, 2002), for guiding light (V. N. Astratov et al., Appl. Phys. Lett. Vol. 83, pp. 5508-5510, 2004) or in biosensing (Vollmer et al., Applied Physics Letters 80, 21, pp. 4057-4059, 2002). The resonances are generated when light, confined by total internal reflection (TIR), orbits near the particle surface and returns in phase after one complete roundtrip (cf. FIG. 2B). The WGM resonances, which can be characterized by the number of wavelengths that fit within an orbit, are extremely sensitive to material added onto the microsphere surface.

Figure 3:
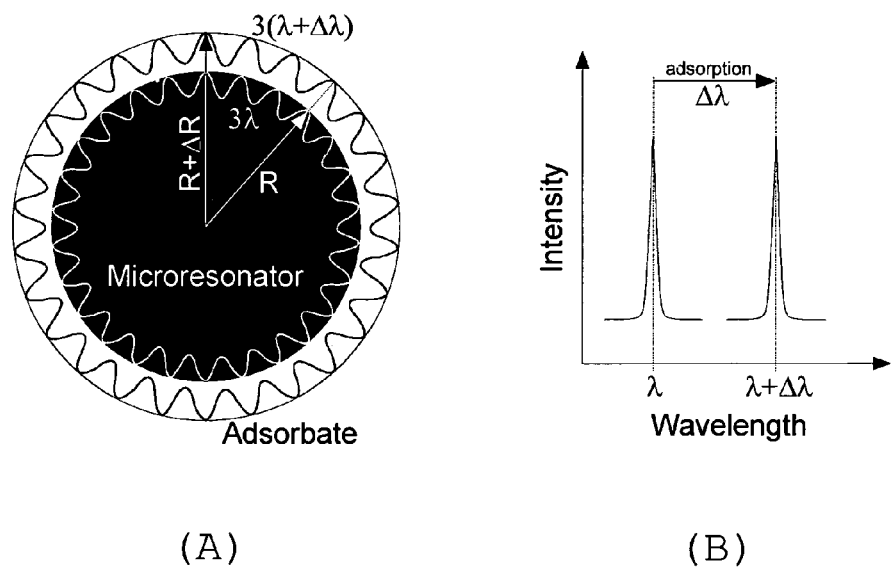

The basic detection scheme that utilizes WGM is that any changes in the parameters defining the microresonator, such as its size, material, refractive index, or refractive index of the environment, change the cavity resonances (G. Schweiger and M. Horn, Journal of the Optical Society of America A, vol. 23, pp. 212-217, 2006). In particular, it was shown that the adsorption of molecules onto the surface of the microresonator (microsphere) induces a change in its WGM spectrum (F. Vollmer et al., Applied Physics Letters 80, pp. 4057-4059, 2002). This change may appear as a wavelength shift of the WGM towards lower or higher wavelengths (blue or red shift) depending on the optical properties of the microsphere's environment and those of the adsorbing molecules. For a microsphere in air, in a simple picture the adsorption of molecules on the microsphere surface can be interpreted as an increase of its radius (FIG. 3A), thus causing a red shift in this case (FIG. 3B). The modes are characterized by the number of wavelengths m that fit into the circumference of the sphere's equator. Assuming that material with same refractive index as the sphere material adsorbs on the surface of the sphere to a final adsorbate layer thickness $\Delta R$, the wavelength $\lambda$ at which the mode can be found then increases by $\Delta\lambda$ due to the increased circumference of the sphere: $\Delta\lambda/\lambda=\Delta R/R$ (FIG. 3B), where R is the radius of the sphere before adsorption of the material.

To ensure specific biosensing, a probe molecule, such as a nucleotide, peptide sequence, antibody or other protein, with sensitivity to a particular ligand (antigen) must be linked to the sphere in such a way that both the probe molecule's functionality and the sphere's Q-factor are preserved. This may also involve the blocking of non-specific adsorption sites as known to those skilled in the art. A thin film of a material with a thickness smaller than the WGMs' evanescent field will not significantly alter the Q-factor of the microresonator; thus, material with a thickness of about 10-100 nm can be deposited on the microsphere while retaining its high Q-factor. It is commonly assumed in the literature that the evanescent field of WGM is of the order of the wavelength of the corresponding mode (Vollmer, 2005, B.I.F. FUTURA, 20, p. 239-244, 2005).

From a practical point of view, the detection of a biomolecule is performed by measuring the WGM of a single isolated microresonator (microsphere in the case of Vollmer et al.) before and after the adsorption of the biomolecule onto the resonator surface. Then a direct comparison of both spectra gives the magnitude of the wavelength shifts of the different WGM, which can be related to the amount of biomolecules adsorbed at the resonator surface. As detailed in the prior arts section, in some cases also the orientation of the adsorbate can be determined by evaluating TE and TM modes separately. Typically, more than a single microresonator will be involved in the measurement, either to improve its accuracy, or to measure a multitude of different binding events simultaneously. Therefore, the necessity of a reference measurement on one and the same resonator requires the recording of its exact location, in particular because the expected size (signal) variation due to (bio-) molecular adsorption is expectedly smaller than the size distribution of the microresonators. Therefore, a single microresonator exhibiting a WGM shift due to biomolecular adsorption cannot be distinguished from one without adsorbed molecules however slightly larger size, thus yielding the same WGM parameters in terms of positions, bandwidths, and intensities. This issue becomes particularly crucial for microresonators freely floating in a medium, such as an aqueous solution, for determination of analyte concentration or (local) refractive indices, stress or flux measurements, and the like, e.g. in microfluidic devices, live cells or tissue, in particular if more than a single sensor is applied.

Figure 7:
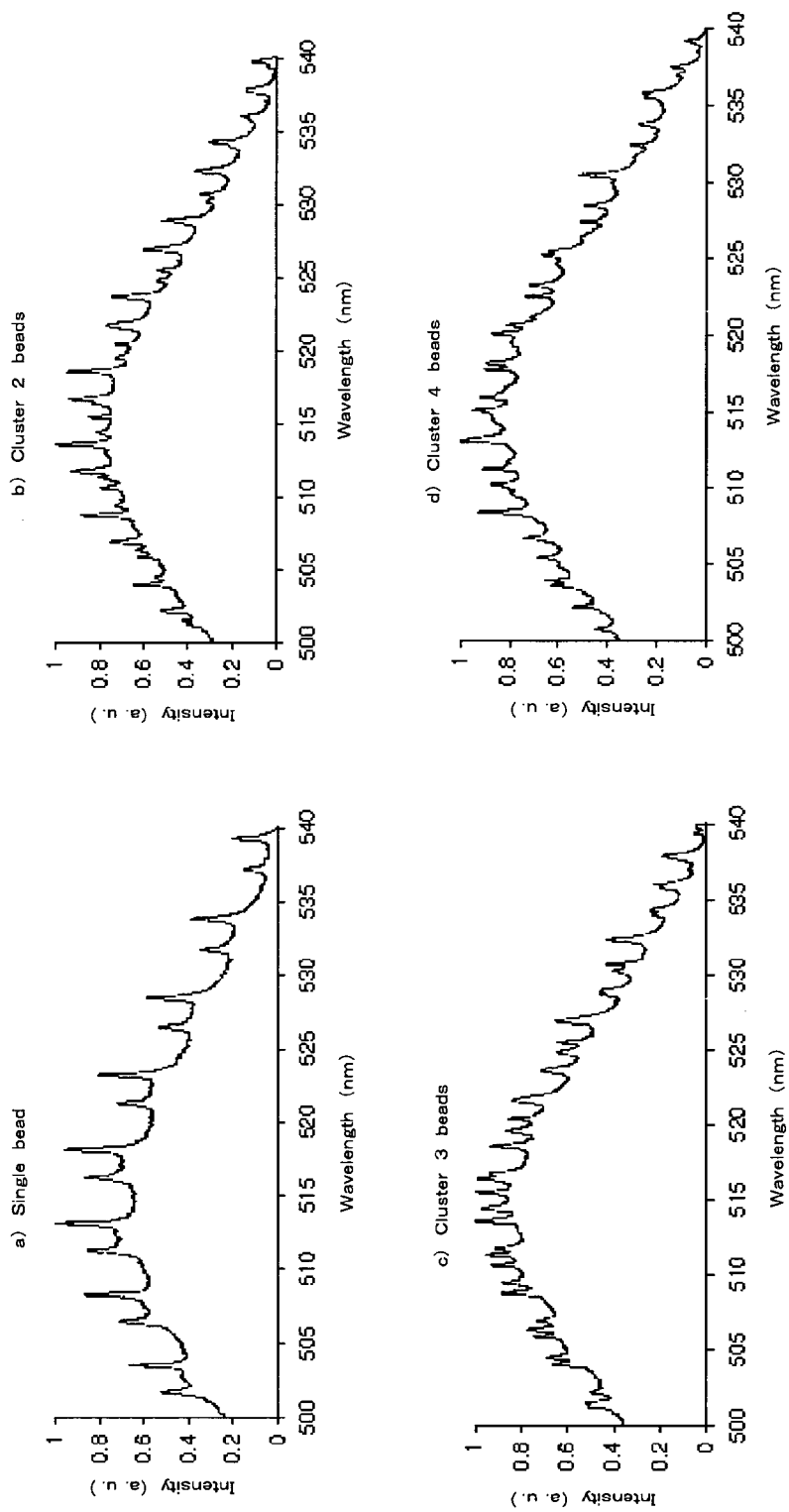

A simple way to overcome these issues is to use clusters of microresonators for sensing instead of single microresonators. Clusters of microspheres can be formed, for example, by depositing a microsphere suspension on a substrate. During the drying process, clusters of different sphere numbers form randomly distributed across the surface. Each cluster is unique in the sense that the probability of finding two clusters on the surface with exactly the same geometry in terms of sphere positions as well as sphere sizes, is basically negligible due to both the standard deviation of the microspheres in the suspension, which is immanent in their fabrication, and the randomness introduced by a basically uncontrolled drying process on surface. Since the WGM parameters (e.g. in terms of mode positions, bandwidths, intensities) of each individual member of the cluster depend on its size as well as the refractive index of its ambient, which is strongly influenced by the position of all other members of the cluster (i.e. the microspheres "sense" each other in a mutual fashion), the WGM spectrum emitted by the cluster as a whole is an almost random and unpredictable superposition of WGM, thus yielding a characteristic overall lineshape. This is in sharp contrast to the utilization of clusters described in the literature (see prior arts section), because there, the main body of work focused on application of microresonators of same size and controlled distance with an aim to achieve mode splitting and related quantum electrodynamic effects, which requires a superposition of cavity modes of same kind within their bandwidths. Accordingly, the randomness introduced in the present embodiment is not suitable for such work. Some work has also been performed utilizing linear chains of microresonators with small (V. N. Astratov et al., Appl. Phys. Lett. Vol. 85, pp. 5508-5510, 2004) and large (V. N. Astratov et al., Appl. Phys. Lett. Vol. 85, pp. 5508-5510, 2004) size mismatch for light guiding purpose. In that work, however, only one of the spheres within a chain was fluorescent, i.e. served as light emitter, so that—despite of the presence of the other microspheres in the chain—basically single-sphere WGM spectra were obtained, with all the implications for sensing applications as discussed above (i.e. a lacking spectral fingerprint). Despite of the size distribution and wanted mismatch of optical cavity modes in the random clusters formed in the present embodiment, accidental mode coupling cannot be excluded a priori, however, it is not the main aspect of the embodiment. Even in the absence of any particular coupling effects between neighboring microresonators, the superposition of optical cavity modes arising from the individual members of the cluster yields a particular lineshape. Therefore, it can be assumed that each cluster of microspheres within a given ensemble of clusters, such as a sample prepared for optical sensing in an array format or a number of clusters freely floating in a fluid medium, exhibits a specific WGM spectrum (at least within the ensemble of interest) that can be considered as its spectral fingerprint due to both the superposition of the WGM spectra of the individual microresonators of different size and varying mutual distance constituting the cluster with their different WGM parameters (such as positions, bandwidths, intensities) and a potential mode coupling that may arise among them. Examples for WGM spectra obtained from a single fluorescent PS particle and from clusters of 2-4 fluorescent PS particles are given in FIG. 7. Obviously, cluster spectra exhibit lower symmetry due to the superposition of the WGM arising from the constituent particles (microresonators).

This scheme of cluster formation takes advantage from the finite size distribution of the colloidal suspension and thus is a very simple and straightforward way to obtain the wanted spectral fingerprints. However, it might also be favorable to apply more advanced procedures of cluster fabrication, e.g. by means of lithographic techniques, and form clusters of microresonators of different type, e.g. of different shape, size, refractive index, coating, and/or fluorescent material. In such sophisticated fabrication of microresonators, e.g. when applying a fabrication technique capable of reproducing structures with high precision, i.e. a technique that achieves only small deviations from the norm (e.g. e-beam or X-ray lithography), the principle of polydispersity, e.g. of a certain size variation or a finite variation of another suitable parameter of the fabricated microresonators for dispersion of their optical cavity mode spectra, may also be introduced artificially. Microresonators of different shape, for example, exhibit typically different cavity mode spectra, e.g. in terms of number and type of modes, resonance positions and bandwidths, thereby possibly reducing the number of excitable modes in the cluster. The resulting simplified mode spectra may facilitate the evaluation of the spectra and/or their storage and processing, and thus help the overall sensing application.

Figure 8:
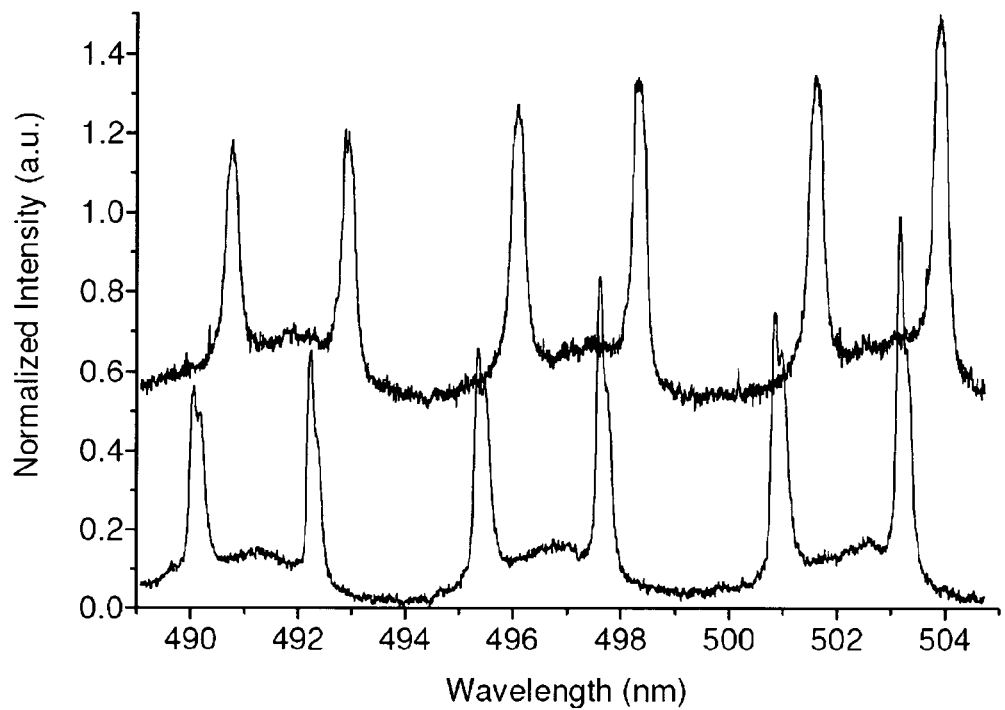
FIG. 8 shows WGM spectra of two single microparticles in Millipore water; spectra vertically displaced for clarity.
Figure 9:
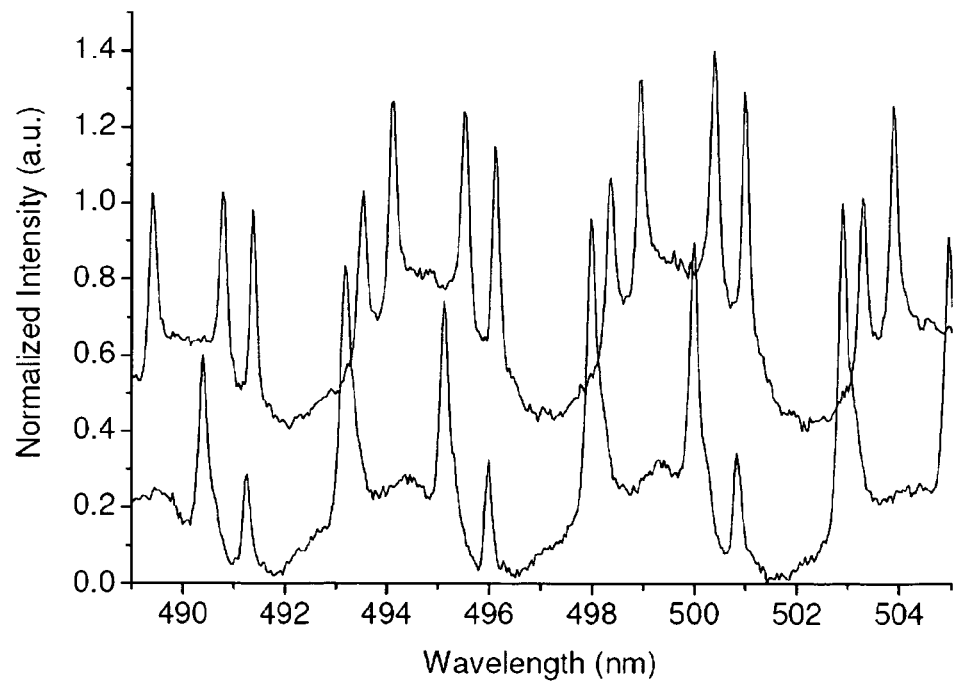
FIG. 9 shows WGM spectra of two different clusters of 2 beads in Millipore water; spectra vertically displaced for clarity.
Figure 10:
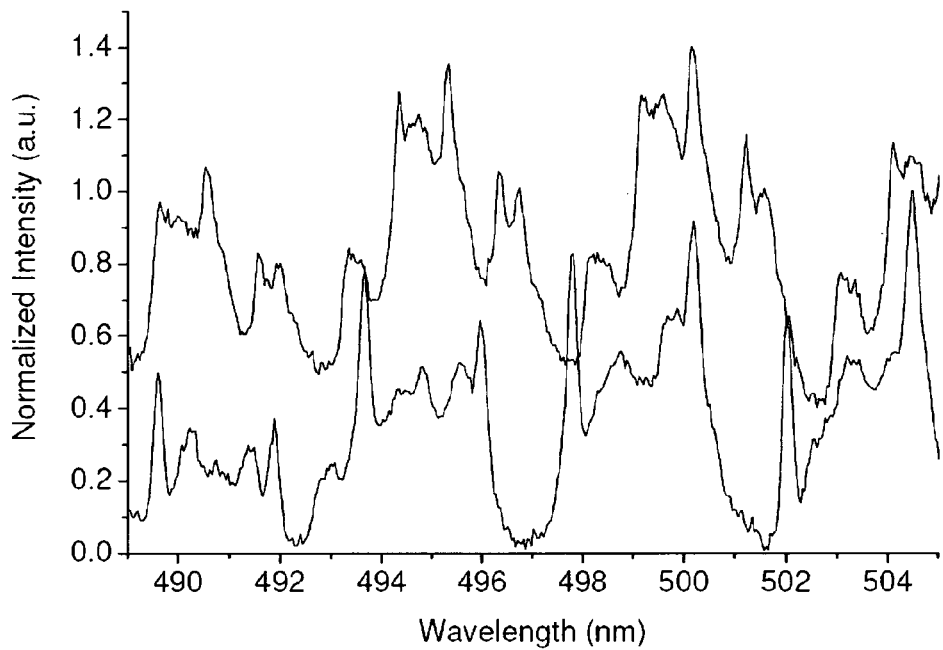
FIG. 10 shows WGM spectra of two different clusters of 3 beads in Millipore water; spectra vertically displaced for clarity.
Figure 11:
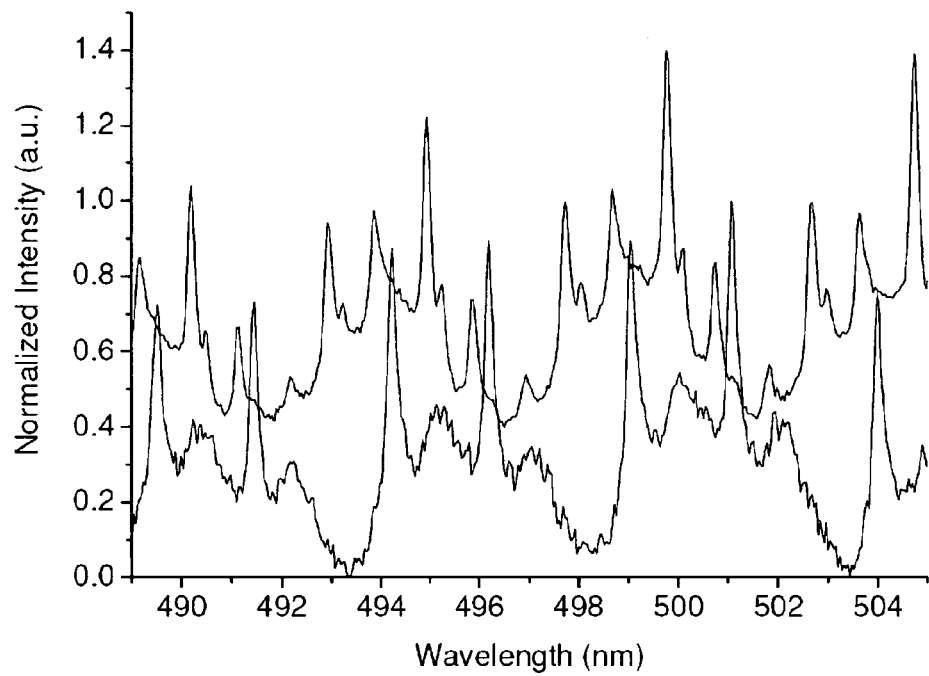
FIG. 11 shows WGM spectra of two different clusters of 4 beads in Millipore water; spectra vertically displaced for clarity.

In the following, we demonstrate the workability of this idea using dye-doped polystyrene microspheres of 10 µm nominal diameter as an example for dielectric microcavities without shell. While the present embodiments may be applicable to clusters of resonators independent of the scheme used for their optical excitation and read-out (e.g. near-field coupling, e.g. by means of an optical fiber, prism coupler, focused laser beam, and the like, or inner excitation by means of Raman emitters, fluorescent dyes, semiconductor quantum dots, semiconductor quantum well structures, and the like), inner excitation schemes seem to be applicable with lesser effort and wider variety (e.g. in the case of freely moving and/or remotely operated clusters). Therefore, as one example for an inner excitation scheme, dye-doped polymer latex particles have been chosen in the following. FIG. 8 shows typical WGM spectra of two single microspheres. It can be seen that both spectra exhibit the same features (number of peaks, spacing between the TE and TM modes, spacing between two consecutive TE or TM modes). Therefore it is not possible to distinguish the two microparticles by means of their WGM spectra, i.e. without proper recording of the spheres' location it is not possible to decide whether the spectra stem from the same sphere before and after adsorption of (bio-)molecules or simply from different spheres. The need for precise positioning, however, puts heavy implications on the development of a commercial sensor system. WGM spectra of clusters of microspheres are shown in FIGS. 9, 10 and 11. In contrast to the single spheres, each spectrum exhibits a unique lineshape even when the clusters contain the same number of microspheres. Thus, even without any recording of the clusters' location, the spectra can be uniquely correlated to the generating cluster.

The most crucial point for the application of the concept of spectral fingerprints in clusters of microresonators to optical sensing is, however, that the fingerprint may not change its overall lineshape in the course of the sensing process, e.g. due to (bio-) molecular adsorption, rather than exhibiting an overall shift in the lineshape of its features. That such overall shift will be observable cannot be assumed a priori, in particular in view of the literature published on mode coupling and waveguiding in linear chains of microresonators, which suggests that e.g. the so-called jet modes (light propagation along the axis defined by the contact points of linear chains of touching microspheres), exhibit different sensitivity to changes in the environmental conditions of the cluster than non-coupled WGM due to their different exposure to the ambient. Surprisingly, however, the inventors of the present embodiment found that down to the adsorption of ultrathin organic films onto the clusters' surface, the main effect of this adsorption is a shift of the clusters' spectral fingerprint spectra as a whole. This is demonstrated in FIGS. 12 and 13, where thin layers of PE were adsorbed on individual microresonators as well as clusters thereof and spectra were recorded before and after adsorption (cf. Example 1 for details), respectively. As it can be clearly seen, the spectrum of the 3-sphere cluster shown in FIG. 13 exhibits simply a shift, while maintaining its overall lineshape. Thus the characteristic fingerprint is preserved during the treatment and the cluster can be easily identified at any time before, during, and after the sensing process.

This approach is highly valuable for the fabrication of arrays of optical (bio-) sensors as it greatly simplifies both the fabrication of the biosensor array itself as well as the detection scheme. The overall substrate can be mapped with respect to WGM spectra without recording the exact position of each cluster. After the adsorption of a (bio-)molecule on the cluster surface, another WGM mapping can be performed across the substrate. Then, despite of a potential wavelength shift, the spectra acquired after biomolecule adsorption can be related to the previously acquired spectra simply by comparing lineshapes. In Example 1 it will be demonstrated that the observable peak shift caused by a defined amount of organic molecules adsorbed on the clusters is independent of the number of microspheres within a cluster and further resembles that of a single microsphere. Consequently, the theory derived for a single microsphere can also be used for clusters in order to characterize the properties of the adsorbed (bio-) molecule. One interesting extension of this approach is the correlation of the spectra before and after the adsorption of the (bio-) molecule by means of an (auto-) correlation function as described in Example 1. The (auto-) correlation does not only identify spectra acquired from the same cluster, it also gives at the same time the average peak shift between the spectra as a result of the calculation. Thus, a (bio-) sensor array based on clusters of microresonators that is processed numerically via an (auto-)correlation function or other kind of suitable mathematical (numerical) algorithm does provide a simple and fast solution for parallel processing of a multitude of (bio-)molecular binding events.

It should be noted once more that while the present example of utilizing fluorescent colloidal particles for cluster formation and sensing is a highly appealing one due to its simplicity, also other kinds of microresonators and in particular other kinds of excitation and detection schemes are applicable. One potential drawback of the present example is, for example, that the microresonators constituting a cluster need to be aggregated in close distance from each other to allow their common detection, which allows the detection of their characteristic spectral fingerprint. This implication may be overcome, for example, by coupling the members of the cluster to a common optical waveguide or other kind of optical coupling device (such as an optical fiber, prism, and the like). In such case, a spectral fingerprint could be obtained, e.g. by tuning a suitable excitation light source coupled into the fiber through the wavelength region of interest and measuring the transmission through the waveguide (cf. e.g. A. Serpengüzel et al., Opt. Lett. 20, pp. 654ff., 1995). Every time, the excitation wavelength matches with a WGM of one of the microresonators coupled to the waveguide, a drop in intensity is observable, which will be again characteristic for the particular system of waveguide and number and kind of microresonators coupled to it, even if the microresonators are positioned well separated from each other. Therefore, the system can be viewed at as a kind of delocalized cluster. Comparison with other systems of same kind will lead to other kinds spectral fingerprints, as long as the dispersion of the microresonators involved is sufficiently high with respect to a suitable parameter, such as microresonator geometry, size, refractive index, dopant, and the like. The feasibility of coupling of more than a single microresonator to an optical fiber has been demonstrated by Vollmer et al. (Biophysical Journal 85, pp. 1974-1979, 2003). The opportunity of utilizing, e.g., size-dispersive microresonators in this configuration for their distinction from other systems of similar kind, e.g. in highly multiplexing waveguide structures, has not been discussed so far. The example above touches also on the timing used for the acquisition of spectral fingerprints. While in the examples below, a CCD camera system has been utilized for fast multichannel detection of WGM spectra, those spectra can also be collected via serial scanning. In above example of utilizing waveguide structures, such serial scanning can be achieved, e.g., by scanning (tuning) the light source (remark: for sufficiently small microresonators with sufficiently large free spectral range (>spectrometer resolution), a parallel detection scheme as facilitated by, e.g., a miniature spectrometer equipped with a linear photodiode array or a monochromator/CCD camera system may be applicable also in the case of waveguide coupling. In such case, the tunable light source may be replaced by a broadband source emitting in the entire wanted spectral range of operation). A further evolution of serial scanning would be to acquire optical cavity mode spectra from the individual members of a cluster and superpose them for example numerically instead of physically. In such case, the need for localizing the cluster as discussed above may become obsolete and a cluster may be defined as an arbitrary suited selection out of an ensemble of microresonators.

Other aspects of the present embodiment relate to the readout of individual microresonators within a given cluster. Examples 3-5 demonstrate how operation of clusters or individual members of a cluster above the lasing threshold does not only significantly improve sensitivity and signal-to-noise ratio of an optical sensing measurement, but further allows the study of individual microresonators within the cluster. Further, as shown in Example 5, also application of more than a single fluorescent material in a cluster of microresonators may be used for the purpose of addressing individual microresonators within the cluster. Besides sensing applications, both schemes offer an interesting opportunity for addressing individual particles, i.e. microresonators, out of a large ensemble. A certain particle could be first addressed by the spectral fingerprint of its host cluster and then, in a second step and due to the fact that the number of members in a cluster is typically small, by its single-particle cavity mode spectrum within that cluster. For further details we refer to the examples below.

Materials Section

The cluster(s) of microresonators of the present embodiment can be manufactured by using materials, which are available to the public. The following explanations of the materials are provided to help those skilled in the art construct the clusters in line with the description of the present specification.

Cavity Material:

Materials that can be chosen for fabrication of the cavity are those which exhibit low absorption in that part of the electromagnetic spectrum, in which the cavity shall be operated. In practice, this is a region of the emission spectrum of the fluorescent material chosen for excitation of the cavity modes. The different cavities of the microresonators involved (constituting the cluster(s)) may be made from different materials and also may be doped with different fluorescent materials, e.g. to allow their selective excitation. Also, the cavities may consist of heterogeneous materials. In one embodiment, the cavities are made from semiconductor quantum well structures, such as InGaP/InGaAlP quantum well structures, which can be simultaneously used as cavity material and as fluorescent material, when pumped with suitable radiation. The typical high refractive index of semiconductor quantum well structures of about 3 and above further facilitates the miniaturization of the cavity or cavities because of the wavelength reduction inside of the semiconductor compared to the corresponding vacuum wavelength. In general, it is advantageous to choose a cavity material of high refractive index to facilitate the miniaturization of the cavities. It is also possible to choose a photonic crystal as cavity material and to coat either the outer surface of the crystal with a fluorescent material, or to embed the fluorescent material into the crystal in a homogeneous or heterogeneous fashion. A photonic crystal can restrict the number of excitable cavity modes, enforce the population in allowed modes, and define the polarization of the allowed modes. The kind of distribution of the fluorescent material throughout the photonic crystal can further help to excite only the wanted modes, while unwanted modes are suppressed due to improper optical pumping.

An example of photonic crystals consisting of two or three-dimensional non-metallic periodic structures that do not allow the propagation of light within a certain frequency range, the so-called "bandgap" of the photonic crystal, was shown by E. Yablonovitch (Scientific American, December issue, pp. 47-55, 2001). The light is hindered from propagation by distributed Bragg diffraction at the periodic non-metallic structure, which causes destructive interference of the differently scattered photons. If the periodicity of such a photonic crystal is distorted by a point defect, e.g. one missing scattering center in the overall periodic structure, spatially confined allowed optical modes within the bandgap may occur, similar to those localized electronic energy levels occurring within the bandgap of doped semiconductors.

In the present embodiment, the optical cavities shown have a spherical shape. Although such spherical shape is a very useful one, the cavity may in principle have any shape, such as oblate spherical shape, cylindrical, or polygonal shape given that the cavity can support cavity modes, as shown in the related art. The shape may also restrict the excitation of modes into a single or a countable number of planes within the cavity volume.

Fluorescent Material:

Optionally, the microresonators and/or optical cavities used for formation of the clusters may be doped with one or more kinds of fluorescent materials to facilitate the excitation of optical cavity mode spectra. In the following, examples of suitable fluorescent materials are given. As fluorescent material, any type of material can be used that absorbs light at an excitation wavelength $\lambda_{exc}$, and re-emits light subsequently at an emission wavelength $\lambda_{em} \neq \lambda_{exc}$. Thereby, at least one part of the emission wavelength range(s) should be located within the mode spectrum of the cavity for whose excitation the fluorescent material shall be used. In practice, fluorescent dyes, semiconductor quantum dots, semiconductor quantum well structures, carbon nanotubes (J. Crochet et al., Journal of the American Chemical Society, 129, pp. 8058-9, 2007), Raman emitters, and the like can be utilized. A Raman emitter is a material that uses the absorbed photon energy partially for excitation of internal vibrational modes and re-emits light with a wavelength higher than that of the exciting light. If a vibration is already excited, the emitted light may also have a smaller wavelength than the incoming excitation, thereby quenching the vibration (anti-Stokes emission). In any case, by proper choice of the excitation wavelength many non-metallic materials may show Raman emission, so that also the cavity materials as described above can be used for Raman emission without addition of a particular fluorescent material. Examples of the fluorescent dyes which can be used in the present embodiment are shown together with their respective peak emission wavelength (unit: nm): PTP (343), DMQ (360), butyl-PBD (363), RDC 360 (360), RDC 360-NEU (355), RDC 370 (370), RDC 376 (376), RDC 388 (388), RDC 389 (389), RDC 390 (390), QUI (390), BBD (378), PBBO (390), Stilbene 3 (428), Coumarin 2 (451), Coumarin 102 (480), RDC 480 (480/470), Coumarin 307 (500), Coumarin 334 (528), Coumarin 153 (544), RDC 550 (550), Rhodamine 6G (580), Rhodamine B (503/610), Rhodamine 101 (620), DCM (655/640), RDC 650 (665), Pyridin 1 (712/695), Pyridin 2 (740/720), Rhodamine 800 (810/798), and Styryl 9 (850/830).

However, for microresonators or clusters thereof which are not coated with a silver shell, any other dye operating in the UV-NIR regime could be used. Examples of such fluorescent dyes are shown: DMQ, QUI, TBS, DMT, p-Terphenyl, TMQ, BPBD-365, PBD, PPO, p-Quaterphenyl, Exalite 377E, Exalite 392E, Exalite 400E, Exalite 348, Exalite 351, Exalite 360, Exalite 376, Exalite 384, Exalite 389, Exalite 392A, Exalite 398, Exalite 404, Exalite 411, Exalite 416, Exalite 417, Exalite 428, BBO, LD 390, α-NPO, PBBO, DPS, POPOP, Bis-MSB, Stilbene 420, LD 423, LD 425, Carbostyryl 165, Coumarin 440, Coumarin 445, Coumarin 450, Coumarin 456, Coumarin 460, Coumarin 461, LD 466, LD 473, Coumarin 478, Coumarin 480, Coumarin 481, Coumarin 485, Coumarin 487, LD 489, Coumarin 490, LD 490, Coumarin 498, Coumarin 500, Coumarin 503, Coumarin 504 (Coumarin 314), Coumarin 504T (Coumarin 314T), Coumarin 510, Coumarin 515, Coumarin 519, Coumarin 521, Coumarin 521T, Coumarin 522B, Coumarin 523, Coumarin 525, Coumarin 535, Coumarin 540, Coumarin 540A, Coumarin 545, Pyrromethene 546, Pyrromethene 556, Pyrromethene 567, Pyrromethene 567A, Pyrromethene 580, Pyrromethene 597, Pyrromethene 597-8C9, Pyrromethene 605, Pyrromethene 650, Fluorescein 548, Disodium Fluorescein, Fluorol 555, Rhodamine 3B Perchlorate, Rhodamine 560 Chloride, Rhodamine 560 Perchlorate, Rhodamine 575, Rhodamine 19 Perchlorate, Rhodamine 590 Chloride, Rhodamine 590 Tetrafluoroborate, Rhodamine 590 Perchlorate, Rhodamine 610 Chloride, Rhodamine 610 Tetrafluoroborate, Rhodamine 610 Perchlorate, Kiton Red 620, Rhodamine 640 Perchlorate, Sulforhodamine 640, DODC Iodide, DCM, DCM Special, LD 688, LDS 698, LDS 720, LDS 722, LDS 730, LDS 750, LDS 751, LDS 759, LDS 765, LDS 798, LDS 821, LDS 867, Styryl 15, LDS 925, LDS 950, Phenoxazone 660, Cresyl Violet 670 Perchlorate, Nile Blue 690 Perchlorate, Nile red, LD 690 Perchlorate, LD 700 Perchlorate, Oxazine 720 Perchlorate, Oxazine 725 Perchlorate, HIDC Iodide, Oxazine 750 Perchlorate, LD 800, DOTC Iodide, DOTC Perchlorate, HITC Perchlorate, HITC Iodide, DTTC Iodide, IR-144, IR-125, IR-143, IR-140, IR-26, DNTPC Perchlorate, DNDTPC Perchlorate, DNXTPC Perchlorate, DMOTC, PTP, Butyl-PBD, Exalite 398, RDC 387, BiBuQ Stilbene 3, Coumarin 120, Coumarin 47, Coumarin 102, Coumarin 307, Coumarin 152, Coumarin 153, Fluorescein 27, Rhodamine 6G, Rhodamine B, Sulforhodamine B, DCM/Pyridine 1, RDC 650, Pyridine 1, Pyridine 2, Styryl 7, Styryl 8, Styryl 9, Alexa Fluor 350 Dye, Alexa Fluor 405 Dye, Alexa Fluor 430 Dye, Alexa Fluor 488 Dye, Alexa Fluor 500 and Alexa Fluor 514 Dyes, Alexa Fluor 532 Dye, Alexa Fluor 546 Dye, Alexa Fluor 555 Dye, Alexa Fluor 568 Dye, Alexa Fluor 594 Dye, Alexa Fluor 610 Dye, Alexa Fluor 633 Dye, Alexa Fluor 647 Dye, Alexa Fluor 660 Dye, Alexa Fluor 680 Dye, Alexa Fluor 700 Dye, and Alexa Fluor 750 Dye.

Water-insoluble dyes, such as most laser dyes, are particularly useful for incorporation into the microresonators, while water-soluble dyes, such as the dyes obtainable from Invitrogen (Invitrogen Corp., Carlsbad, Calif.), are particularly useful for staining of their environment or their outer surface.

Semiconductor quantum dots that can be used as fluorescent materials for doping the microresonators have been described by Woggon and coworkers (M. V. Artemyev & U. Woggon, Applied Physics Letters 76, pp. 1353-1355, 2000; M. V. Artemyev et al., Nano Letters 1, pp. 309-314, 2001). Thereby, quantum dots (CdSe, CdSe/ZnS, CdS, CdTe for example) can be applied to the present embodiment in a similar manner as described by Kuwata-Gonokami and coworkers (M. Kuwata-Gonokami et al., Jpn. J. Appl. Phys. Vol. 31, pp. L99-L101, 1992), who have shown that the fluorescence emission of dye molecules can be utilized for population of cavity modes of microresonators. The major advantage of quantum dots over dye molecules is their higher stability against degradation, such as bleaching. The same argument holds for semiconductor quantum well structures, e.g. structures made from InGaP/InGaAlP, which exhibit high stability against bleaching and cannot only be used as fluorescent material but also as cavity material.

The excitation wavelength $\lambda_{exc}$ of the fluorescent material does not have necessarily to be smaller than its emission wavelength $\lambda_{em}$, i.e. $\lambda_{exc} < \lambda_{em}$, since one also can imagine multiphoton processes, where two or more photons of a given energy have to be absorbed by the material before a photon of twice or higher energy will be emitted. Also, as mentioned above, Raman anti-Stokes processes might be used for similar purpose.

In general, the fluorescent material can be incorporated into the cavity material or be adsorbed on its surface. The distribution can be used to select the type of cavity modes that are excited. For example, if the fluorescent material is concentrated in vicinity of the core surface, whispering gallery modes are more likely to be excited than Fabry Perot modes. If the fluorescent material is concentrated in the centre of the cavity, Fabry Perot modes are easier to excite. Other examples of a heterogeneous distribution are those, in which the fluorescent material is distributed in an ordered fashion, i.e. in terms of regular two- or three-dimensional patterns of volumes with a high concentration of the fluorescent material. In such a case, diffraction effects may occur, which help to excite the cavity in distinct directions, polarizations, and/or modes, e.g., similar to those found in distributed feedback dye lasers.

Shell:

The cavity/cavities and/or the cluster(s) of microresonators may be embedded in a shell which may have a homogeneous or heterogeneous thickness (e.g. holey) and/or homogeneous or heterogeneous composition. In the case of inner cavity excitation by means of a fluorescent material, the shell may consist of any material (metal, dielectric, semiconductor) that shows sufficient transmission at the excitation wavelength $\lambda_{exc}$ of the chosen fluorescent material(s). Also, the shell may consist of different materials with wanted properties, for example to render the surface of the microresonator(s) and/or cluster(s) of microresonators transparent only at wanted locations and/or areas or—to give another example—to facilitate material selective (bio-)functionalization. In the case of semiconductors, the shell becomes transparent when the excitation wavelength is higher than the wavelength corresponding to the bandgap of the considered semiconductor. For a metal, high transparency may be achieved, for example, by taking advantage of the plasma frequency of the metal, above which the conduction electrons of the metal typically do no longer contribute to the absorption of electromagnetic radiation. Among useful metals are aluminum and transition metals, such as silver, gold, titanium, chromium, cobalt and the like. The shell may be continuous, as fabricated for example via evaporation or sputtering, or contiguous (or holey) as often achieved by means of colloidal metal particle deposition and subsequent electroless plating (Braun & Natan, Langmuir 14, pp. 726-728, 1998; Ji et al., Advanced Materials 13, pp. 1253-1256, 2001; Kaltenpoth et al., Advanced Materials 15, pp. 1113-1118, 2003). In the case that the shell is utilized for light confinement (cf. e.g. PCT/JP2007/059443), the thickness of the shell may vary from few nanometers to several hundreds of nanometers. The only stringent requirement for this purpose is that the reflectivity of the shell is sufficiently high in the wanted spectral range to allow for Q-factors with values of Q>1. For FPM in spherical cavities, the Q-factor can be calculated from the reflectance of the shell 4 (or vice versa) by the formula $$Q = \frac{\lambda_m}{\Delta \lambda_m} = m\pi \frac{\sqrt{R_{sh}}}{1 - R_{sh}} \tag{4}$$

where $R_{sh}$ is the reflectance of the shell and $\lambda_m$ the wavelength of cavity mode m.

Biofunctional Coating:

The cluster(s) of microresonators and/or optical cavities may be coated with a (bio-)functional coating facilitating their (bio-)mechanical and/or (bio-) chemical function. For example, they may be functionalized with specific analytes to initiate a wanted cell response, or to facilitate biomechanical and/or biochemical sensing. Also individual microresonators and/or optical cavities within a cluster may be coated with a (bio-) functional coating. In such case, they may bear different coatings, e.g. for detecting different analytes or for providing a reference or control. For sake of brevity, the coated microresonator(s) (optical cavity/ies) and/or cluster(s) of microresonators (optical cavities) will be called "the sensor" in the following.

To render the sensor selective for specific analytes, it is preferred to coat the sensor surface with coupling agents that are capable of (preferably reversibly) binding an analyte, such as proteins, peptides, and nucleic acids. Methods for conjugating coupling agents are well-known to those skilled in the art for various kinds of surfaces, such as polymers, inorganic materials (e.g. silica, glass, titania) and metal surfaces, and are equally suitable for derivatizing the sensor surface of the present embodiments. For example, in the case of a transition metal-coating (e.g. gold, silver, copper, and/or an alloy and/or composition thereof), the sensor of the present embodiments can be chemically modified by using thiol chemistries. For example, metal-coated non-metallic cores can be suspended in a solution of thiol molecules having an amino group such as aminoethanethiol so as to modify the sensor surface with an amino group. Next, biotin modified with N-hydroxysuccinimide suspended in a buffer solution of pH 7-9 can be activated by EDC, and added to the sensor suspension previously modified by an amino group. As a result, an amide bond is formed so as to modify the metal-coated non-metallic cores with biotin. Next, avidin or streptavidin comprising four binding sites can be bound to the biotin. Next, any biotin-derivatized biological molecule such as protein, peptide, DNA or any other ligand can be bound to the surface of the avidin-modified metal-coated non-metallic cores.

Alternatively, amino-terminated surfaces may be reacted with an aqueous glutardialdehyde solution. After washing the sensor suspension with water, it is exposed to an aqueous solution of proteins or peptides, facilitating covalent coupling of the biomolecules via their amino groups (R. Dahint et al., Anal. Chem., 1994, Vol. 66, pp. 2888-2892). If the sensor is first carboxy-terminated, e.g. by exposure to an ethanolic solution of mercaptoundecanoic acid, the terminal functional groups can be activated with an aqueous solution of EDC and N-hydroxysuccinimide. Finally, proteins or peptides are covalently linked to the activated surface via their amino groups from aqueous solution (Herrwerth et al., Langmuir 2003, Vol. 19, pp. 1880-1887).

In a similar fashion, also non-metallic sensors can be specifically functionalized. For example, PE, such as PSS, PAA, and PAH, can be used as described in the literature (G. Decher, Science Vol. 277, pp. 1232ff., 1997; M. Lösche et al., Macromol. Vol. 31, pp. 8893ff., 1998) to achieve a sensor surface comprising a high density of chemical functionalities, such as amino (PAH) or carboxylic (PAA) groups (this technique is also applicable to metal-coated sensors). Then, for example the same coupling chemistries as described above can be applied to these PE coated sensors. Alternatively, and in analogy to the thiol chemistry described above for functionalization of metal surfaces, suitable kinds of coupling agents, such as amino-, mercapto-, hydroxy-, or carboxy-terminated siloxanes, phosphates, amines, carboxylic or hydroxamic acids, and the like, can be utilized for chemical functionalization of the sensor surface, on which basis then coupling of biomolecules can be achieved as described in the examples above. Suitable surface chemistries can be found in the literature (e.g. A. Ulman, Chem. Rev. Vol. 96, pp. 1533-1554, 1996).

A general problem in controlling and identifying biospecific interactions at surfaces and particles is non-specific adsorption. Common techniques to overcome this obstacle are based on exposing the functionalized surfaces to other, strongly adhering biomolecules in order to block non-specific adsorption sites (e.g. to BSA). However, the efficiency of this approach depends on the biological system under study and exchange processes may occur between dissolved and surface bound species. Moreover, the removal of non-specifically adsorbed biomolecules may require copious washing steps, thus, preventing the identification of specific binding events with low affinity.

A solution to this problem is the integration of the coupling agents into inert materials, such as coatings of poly-(PEG) and oligo(ethylene glycol) (OEG). The most common technique to integrate biospecific recognition elements into OEG-terminated coatings is based on co-adsorption from binary solutions, composed of protein resistant EG molecules and a second, functionalized molecular species suitable for coupling agent coupling (or containing the coupling agent itself). Alternatively, also direct coupling of coupling agent to surface-grafted end-functionalized PEG molecules has been reported.

Recently, a COOH-functionalized poly(ethylene glycol) alkanethiol has been synthesized, which forms densely-packed monolayers on gold surfaces. After covalent coupling of biospecific receptors, the coatings effectively suppress non-specific interactions while exhibiting high specific recognition (Herrwerth et al., Langmuir 2003, Vol. 19, pp. 1880-1887).

The binding entities immobilized at the surface may be proteins such as antibodies, (oligo-)peptides, oligonucleotides and/or DNA segments (which hybridize to a specific target oligonucleotide or DNA, e.g. a specific sequence range of a gene, which may contain a single nucleotide polymorphism (SNP), or carbohydrates). To reduce non-specific interactions, the binding entities will preferably be integrated in inert matrix materials.

Position Control Functionality:

The sensors of the present embodiments may be utilized as remote sensors and therefore may require control of their positions and/or movements by external means, for example to control their contact and/or interaction with a selected cell. Such control may be achieved by different means. For instance, the sensors which are rendered magnetic and electromagnetic forces may be applied to direct the sensor(s) (C. Liu et al., Appl. Phys. Lett. Vol. 90, pp. 184109/1-3, 2007). For example, paramagnetic and super-paramagnetic polymer latex particles containing magnetic materials, such as iron compounds, are commercially available from different sources (e.g. DynaBeads, Invitrogen Corp., or BioMag/ProMag microspheres, Polysciences, Warrington, Pa.). Because the magnetic material is embedded into a polymeric matrix material, which is typically made of polystyrene, such particles may be utilized in the same or a similar way as optical cavity mode sensors as the non-magnetic PS beads described in the examples below. Alternatively or in addition, a magnetic material/functionality may be borne by the shell of the microresonator(s) and/or their (bio-)functional coating or may be introduced through (separate) magnetic particles added to the cluster(s) of microresonators.

Further, the position control may be mediated by means of optical tweezers (J. R. Moffitt et al., Annu Rev. Biochem. Vol. 77, pp. 205-228, 2008). In such case, the laser wavelength(s) of the optical tweezers may be either chosen such that it does or that it does not coincide with excitation and/or emission wavelength range(s) of the fluorescent material(s) used to operate the sensor. For example, it might be desirable to use the optical tweezers' operating wavelength also for (selective) excitation of (one of) the fluorescent material(s). One advantage of optical tweezers over magnetic tweezers would be that a number of different sensors may be controlled individually at the same time (C. Mio et al., Rev. Sci. Instr. Vol. 71, pp. 2196-2200, 2000).

In other schemes, position and/or motion of the sensors may be controlled by acoustic waves (M. K. Tan et al., Lab Chip Vol. 7, pp. 618-625, 2007), (di)electrophoresis (S. S. Dukhin and B. V. Derjaguin, "Electrokinetic Phenomena", John Wiley & Sons, New York, 1974; H. Morgan and N. Green, "AC Electrokinetics: colloids and nanoparticles", Research Studies Press, Baldock, 2003; H. A. Pohl, J. Appl. Phys. Vol. 22, pp. 869-671, 1951), electrowetting (Y. Zhao and S. Cho, Lab Chip Vol. 6, pp. 137-144, 2006), and/or by a microfluidics device that potentially may also be capable of sorting/picking particles and/or cells of desired dimension and/or function (S. Hardt, F. Schonfeld, eds., "Microfluidic Technologies for Miniaturized Analysis Systems", Springer, N.Y., 2007).

Also mechanical tweezers may be utilized for position control of the sensor(s), for example by employing a microcapillary capable of fixing and releasing particles via application of pressure differences (M. Herant et al., J. Cell Sci. Vol. 118, pp. 1789-1797, 2005). The beauty of this approach is that for example in cell sensing experiments, sensors and cells may be manipulated using the same instrumentation (cf. M. Herant et al.). Also combinations of two or more of the schemes described above may be suitable for position control of sensor(s) and/or cell(s).

Excitation Light Source:

The cluster(s) of microresonators and/or optical cavities may be excited in different ways, such as methods of evanescent field coupling or by means of fluorescent materials. These methods have been vastly presented and discussed in the literature with respect to excitation of optical cavity modes in single microresonators and/or optical cavities (A. N. Oraevsky, Quant. Electron. Vol. 32, 377-400, 2002; K. J. Vahala, Nature 424, pp. 839-846, 2003; A. B. Matsko and V.

S. Ilchenko, IEEE J. Sel. Top. Quant. Electron. Vol. 12, 1, pp. 3-14, 2006; M. Kuwata-Gonokami et al., Jp. J. Appl. Phys., Vol. 31, pp. L99-L101, 1992; F. Vollmer and S. Arnold, Nature Meth. Vol. 5, 591ff., 2008; A. Weller et al. Appl. Phys. B Vol. 90, pp. 561-567, 2008) and can be extended in a straightforward fashion to the operation of clusters by those skilled in the art. In the case of evanescent field coupling, the light source(s) may be chosen such to emit suitable radiation (e.g. with suitable bandwidth, intensity and/or collimation) within the wanted spectral range of operation of the microresonators and/or optical cavities constituting the cluster(s). In the case of use of fluorescent material(s), a light source has to be chosen such that its emission falls into the excitation frequency range $\omega_{exc}$ of the fluorescent material(s). In general, the emission power should be such that it can overcompensate the losses (radiation losses, damping, absorption, scattering) that may occur in the course of excitation of the microresonators and/or optical cavities. In practice, thermal sources, such as tungsten or mercury lamps may be applied. Lasers or high power light emitting diodes with their narrower emission profiles will be preferably applied to minimize heating of sample and environment. Also, tunable light sources may be of interest, e.g. for serial excitation of different microresonators and/or optical cavities within a cluster by use of different fluorescent materials and/or by evanescent field coupling. In such case the application of tunable light sources with sufficiently narrow bandwidth to allow optical cavity mode separation may be preferable. If several fluorescent materials are utilized with suitably chosen, e.g. non-overlapping, excitation frequency ranges, more than a single light source may be chosen such that individual clusters of microresonators and/or individual microresonators within a cluster may be addressed selectively, e.g. to further facilitate the readout process or for the purpose of reference measurements (cf. Example 5). The light source(s) may be equipped with suitable filters and/or other means of wavelength selecting instrumentation (e.g. beamsplitters, dispersive elements, apertures) to serve the purpose of proper excitation of the microresonators while reducing unwanted side effects (e.g. for excitation wavelength range selection, suppression of radiative heating and/or radiation-induced damage). Further, the excitation power of at least one of the light sources may be chosen such that at least one of the microresonator(s) within a cluster and/or at least one of the clusters of microresonators utilized is/are operated—at least temporally—above the lasing threshold of at least one of the optical cavity modes excited.

Detection of Fluorescence Emission:

For detection of optical cavity mode spectra from clusters of microresonators and/or optical cavities, any kind of light collection optics known to those skilled in the art may be utilized. For example, the emission from the microresonators and/or optical cavities or clusters thereof can be collected by a microscope objective of suitable numerical aperture and/or any other kind of suitable far-field optics, by an optical fiber, a waveguide structure, an integrated optics device, the aperture of a near field optical microscope (SNOM), or any suitable combination thereof. In particular, the collection optics may utilize far-field and/or near-field collection of the signal. Light collection may be performed from the entire cluster simultaneously or in a serial fashion, e.g. from subsets or even from the individual members of the cluster one by one. In the latter cases, the different signals may be superposed (e.g. electronically or numerically, e.g. also in a later stage of the analysis or evaluation of the measurements) to obtain a spectral fingerprint. The collected light can be analyzed by any kind of suitable spectroscopic apparatus operating in parallel (multichannel) or serial acquisition mode (single channel). For example, confocal fluorescence microscopes combine fluorescence excitation via laser light with collection of the fluorescence emission with high numerical aperture, followed by filtering and spectral analysis of the fluorescence emission. Since such instruments are often used in cell studies, they may provide a convenient tool for implementation of the present embodiments. Other convenient instruments are, for example, Raman microscopes, which also combine laser excitation and high numerical aperture collection of light signals from microscopic sources with spectral analysis. Further, both kinds of instruments allow simultaneous spectral analysis and imaging, which facilitates tracing of individual microresonators and/or clusters of microresonators while tracing their optical response. If such imaging information is not required, also other kinds of spectroscopic devices, such as monochromators, (miniature) spectrometers, fluorescence plate readers, and the like, may be applicable.

Embodiment 1

Figure 5:
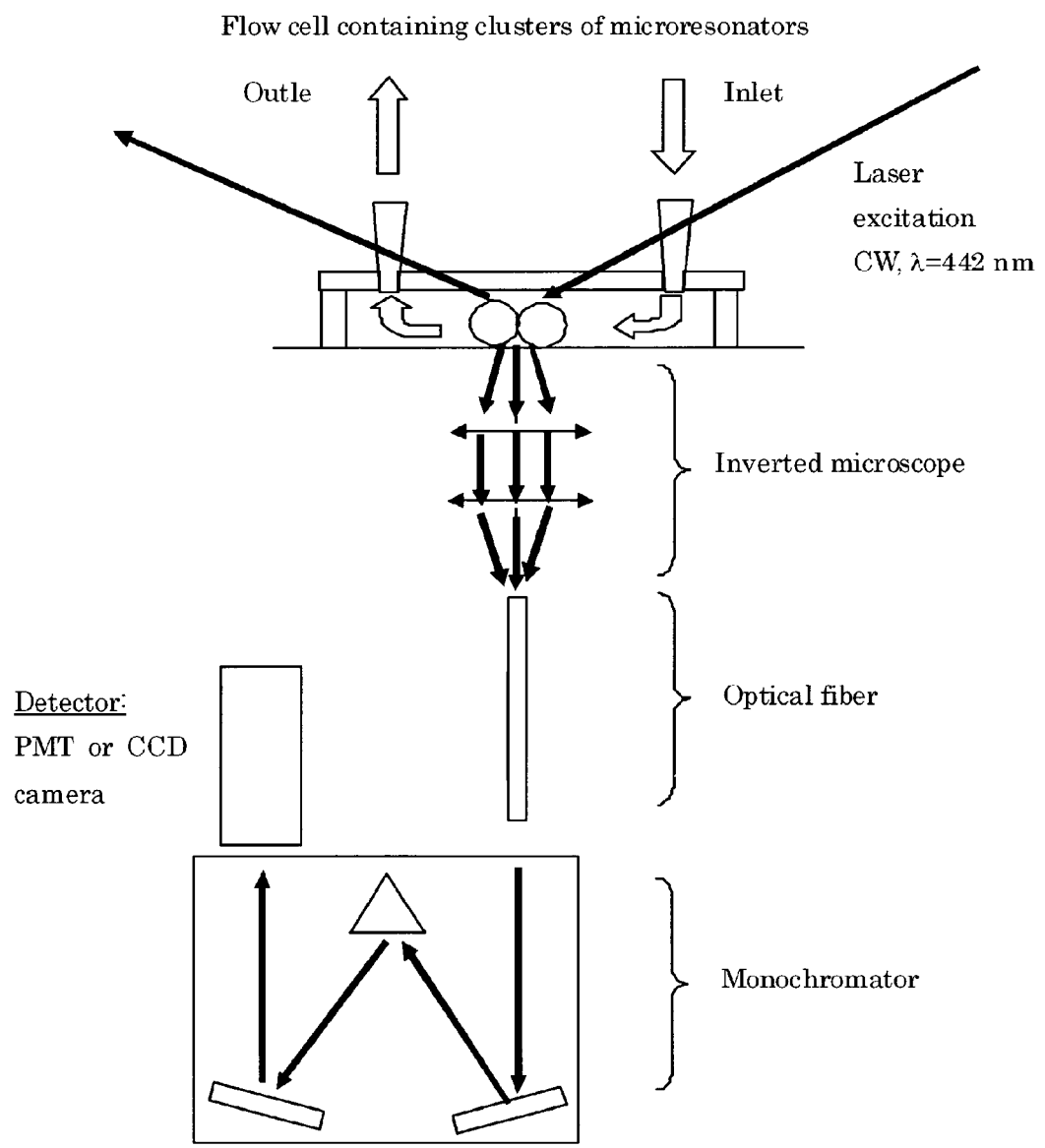
FIG. 5 is a schematic view that depicts an experimental setup used for measuring the WGM emitted by clusters of microparticles.

Optical Sensor Based on a Single Cluster of Microresonators for Molecular Detection An optical sensor consisting of a cluster of microresonators in the sense defined above is placed into a microfluidic flow cell as exemplified in FIG. 5. The number of microresonators has to be superior or equal to 2 in order to form a cluster. The microresonators can be functionalized in order to promote a specific interaction with a particular (bio-)molecule. For sensing, the following detection scheme has to be pursued.

1. Measurement of the WGM spectrum of the cluster of microresonators in the flow cell after introduction of the probe molecule and potential passivation of non-specific binding sites on the cluster surface, however prior to any exposure to the wanted target molecule.

2. Exposure of the cluster to an analyte containing the wanted target molecule.

3. Measurement of the WGM spectrum of the cluster after exposure to the target molecule.

4. By direct comparison of both WGM spectra, before and after the adsorption of the (bio-)molecule, the magnitude of the WGM wavelength shift can be determined and then related to the presence of the target molecule in solution. The analysis of the data can be performed by autocorrelation of the two WGM spectra measured before and after the adsorption of the biomolecule as detailed in Example 1.

Embodiment 2

Figure 19:
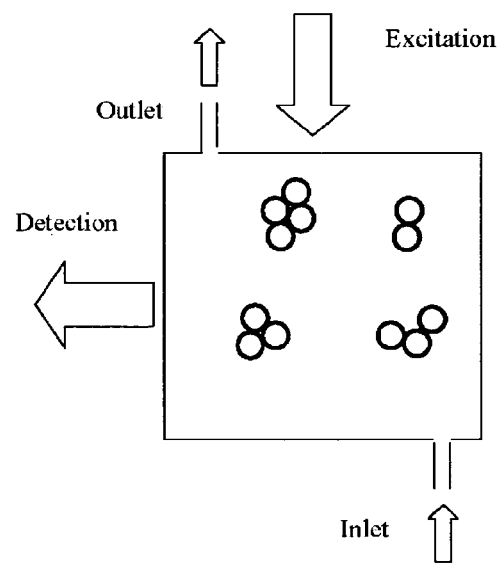
FIG. 19 is a schematic view that depicts clusters of microresonators floating in a microfluidic flow cell.

Optical Sensor Based on an Array of Clusters of Microresonators for Molecular Detection An optical sensor consisting of an array of clusters of microresonators, which are positioned in such a way that the microresonators are forming multiple clusters, is placed into a microfluidic flow cell. The microresonators can be deposited randomly on a substrate (FIG. 18A) or in an ordered fashion (FIG. 18B) or can float freely in the microfluidic flow cell (FIG. 19). The number of microresonators in each cluster has to be superior or equal to 2. The microresonators can be (bio-)chemically modified in order to ensure specific binding of a (bio-)molecule. The different clusters are independent from each other (e.g. in terms of materials composition and shape). The different microresonators and/or clusters may also be differently (bio-)functionalized to allow for multiple sensing or for reference purpose, for example, some of the microresonators and/or clusters bear a first probe molecule for detecting a first target molecule while other microresonators and/or clusters bear a second probe molecule for detecting a second target molecule different from the first one. For (bio-) sensing, the following detection scheme has to be pursued.

1. Measurement of WGM spectra of the clusters of microresonators in the flow cell after introduction of one or more (different) probe molecules and potential passivation of non-specific binding sites on the cluster surface, however prior to any exposure to the wanted target molecule(s).
2. To obtain spectra from all clusters, an image scan of the surface or volume bearing the clusters can be recorded at once or in a sequence of measurements.
3. Exposure of the cluster to an analyte containing the wanted target molecule(s).
4. Measurement of the WGM spectra of all clusters of microresonators after the exposure to the wanted target molecule as described before.
5. By direct comparison of both kinds of WGM spectra, before and after the adsorption of the (bio-)molecule, the magnitude of the WGM wavelength shift can be determined and then related to the presence of the target molecule(s) in solution. Assuming that each cluster is unique and exhibits a WGM spectrum that can be considered as its fingerprint, it is possible to identify a specific WGM spectrum before and after analyte exposure. The analysis of the data can be performed by using an autocorrelation function as described above as well as in more detail in Example 1.

Embodiment 3

Optical Biosensor Based on Arrays of Clusters of Microresonators with a Variety of Shapes for the Detection of a Specific Biomolecule An optical sensor consisting of an array of clusters of microresonators placed into a microfluidic flow cell. The considered microresonators may have different geometry, e.g. spherical, cylindrical, disc or ring shape and the like, as long as they allow for excitation of cavity modes. The sensor may consist of microresonators with homogeneous shape (only spheres, rings, cylinders, and so on) or can be a heterogeneous mixture of two or more types of microresonators with different shapes (spheres and cylinders for example). The cluster-forming microresonators can be deposited randomly on a substrate or be suspended in solution. The number of microresonators in a single cluster has to be superior or equal to 2 in order to form a cluster and the surface of the microresonators may be functionalized in order to ensure specific binding of a (bio-)molecule. The different clusters deposited on the substrate are independent from each other, for example in view of materials choice, spectral range of excitation and readout, and/or their functionalization. For biosensing, the detection scheme presented in the Embodiment 2 can be applied.

Example 1

Adsorption of Layers of Polyelectrolyte on Individual Microresonators and Clusters of Microresonators In the following example, multiple layers of PE were deposited on single microperes as well as clusters of microspheres. The WGM wavelength shift induced by the adsorption of the PE layers was determined after each deposition step. As WGM sensors, Coumarin 6G (C6G)-doped polystyrene (PS) beads with a nominal diameter of 10 µm were utilized. The experimental setup for the acquisition of the WGM spectra is detailed in FIG. 5. The microspheres are first deposited on a PAH-coated microscopy cover slip via drop coating, where they are immobilized by means of electrostatic interactions with the surface in order to ensure that location and configuration of the clusters remain the same throughout the entire experiment. Then, a flow cell is built around the deposited beads. The excitation of the laser dye inside the microspheres is achieved by means of a cw HeCd laser emitting at 442 nm. The fluorescence light scattered from the spheres is collected by a 100× objective mounted to an inverted microscope (Nikon TS 100), and then guided to a monochromator (Jobin-Yvon Triax 550) via an optical fiber. The detection of the signal is carried out by either a CCD camera or a photomultiplier positioned at the monochromator exit.

Figure 6:
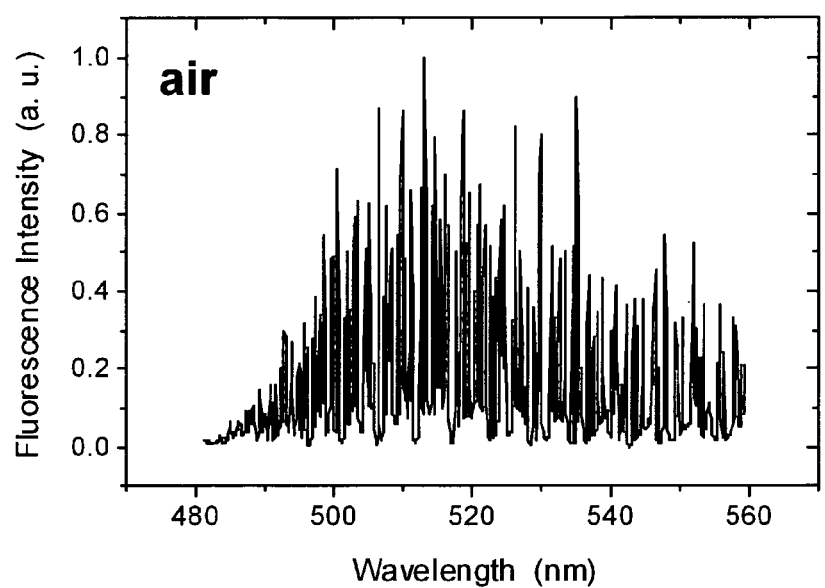
Figure 6:
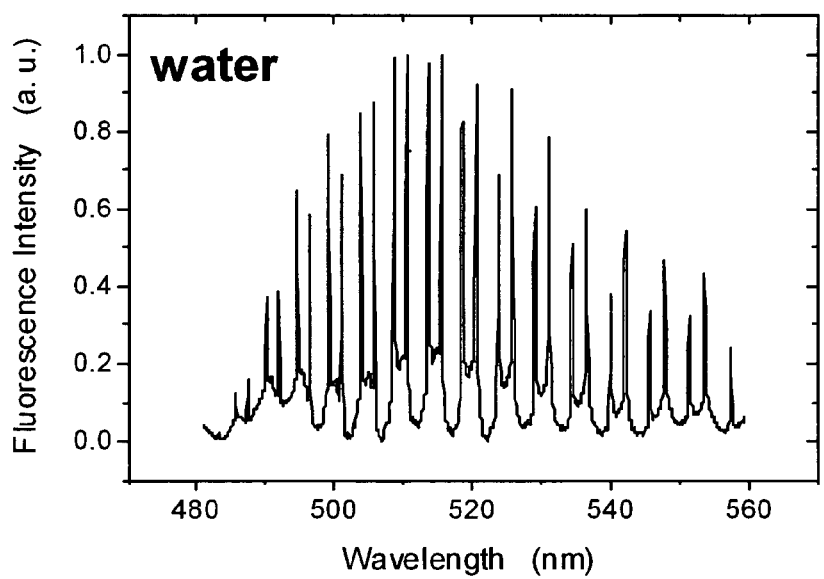

A typical WGM spectrum of a single bead measured in a dry environment is shown in FIG. 6A. Many peaks can be seen, which correspond to a variety of excited optical modes within the microbead of differing mode number and mode order (for details, see, e.g., A. N. Oraevsky, Quantum Electronics Vol. 32, 377-400, 2002). However, when the same microparticle is measured in water (FIG. 6B), the fluorescence spectrum is greatly simplified. The reason is that due to the increased refractive index of the sphere's environment, the conditions for total internal reflection have changed and only those modes with highest Q-factors survive under these harsher conditions. These modes are typically those with the largest radii of curvature with respect to their trajectories, i.e. those traveling in immediate proximity of the sphere's equator. Such modes are called $1^{st}$ order modes or $q=1$ modes in the literature (cf., eg., A. N. Oraevsky). Since the fluorescence emission of the dye is non-polarized, WGM of different polarization may be excited, which can be classified as TE and TM modes, respectively. Thus, the spectrum of FIG. 6 shows both TE and TM modes for different quantum numbers m, i.e. for different multiples of the wavelength (cf. eq. 3).

FIGS. 7-11 compare both the WGM spectra of a single microsphere as well as of clusters of multiple microspheres immersed in water. From these spectra it can be seen that clusters (FIGS. 7B, 7C, 7D, and 9-11) exhibit spectra with completely different lineshape depending on their composition, i.e. number of microspheres present in the cluster, microsphere radii, and arrangement of spheres within the cluster. The more complex structure of the WGM spectra of clusters is associated with the fact that WGM spectra of the individual microspheres in the cluster are superposing, and that in addition coupling effects between different microspheres may occur such as described above.

Figure 12:
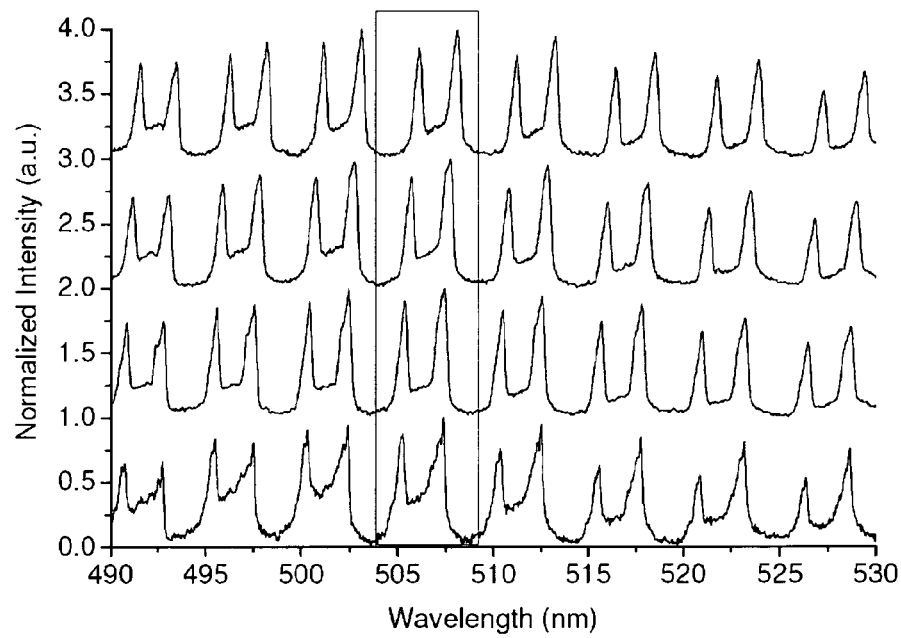
Figure 12:
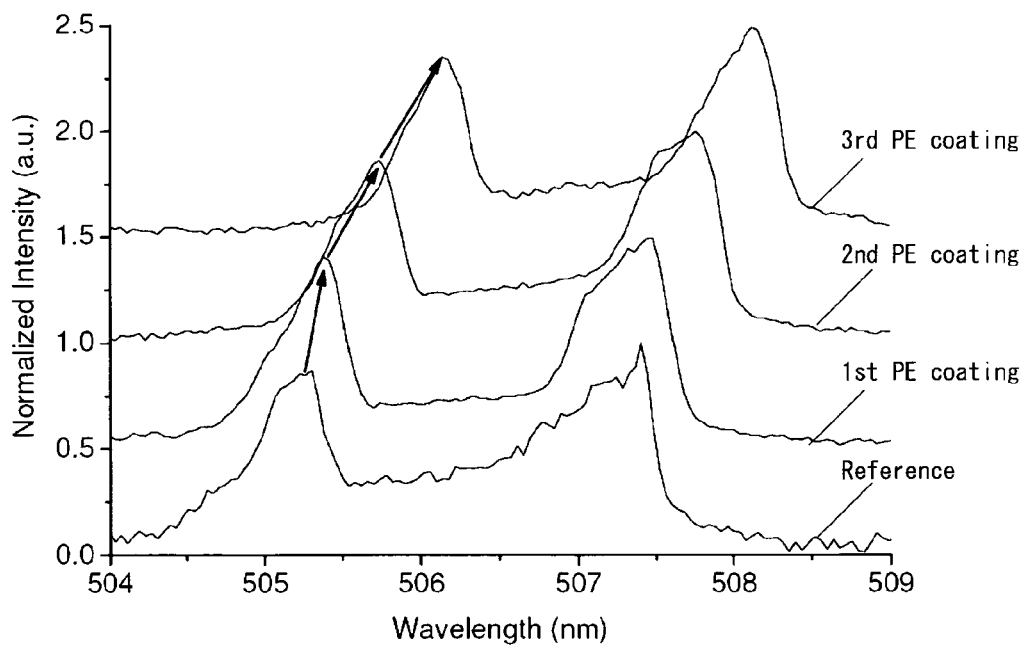
Figure 13:
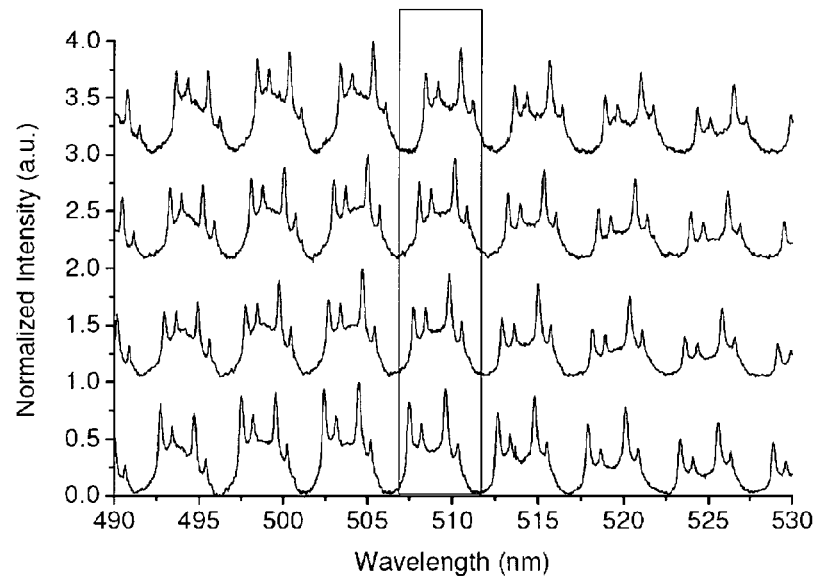
Figure 13:
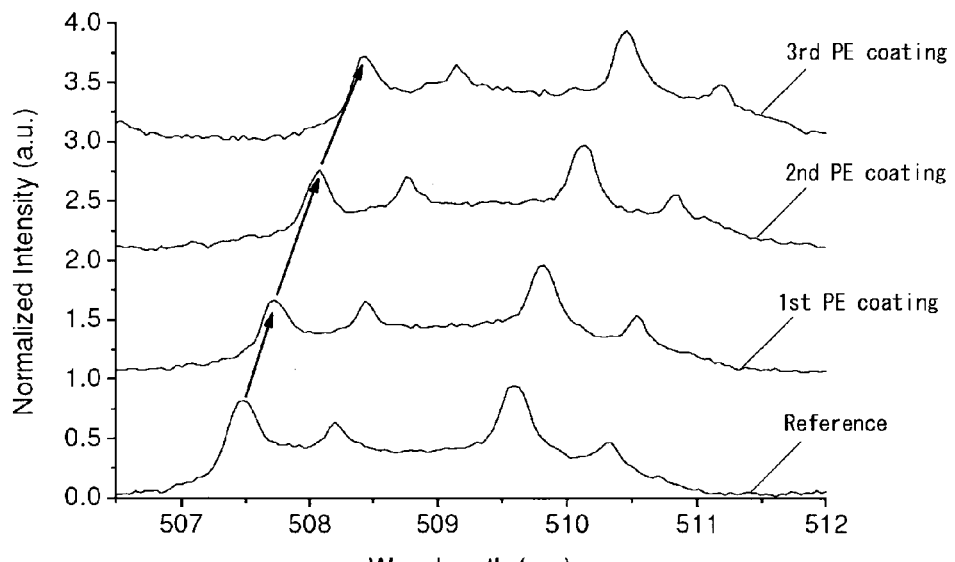

PE form thin organic films of well-defined thickness and thus provide a very interesting system for testing the potential of WGM excitations in clusters of microspheres for sensing applications. Multiple layers of polyelectrolyte (PSS and PAH) can be easily deposited on the microparticle surface using the Layer-by-Layer (LbL) deposition process described elsewhere (G. Decher, Science 277, pp. 1232-1237, 1997). Measurements of the WGM were performed in situ in the flow cell, as depicted in FIG. 5, between the successive deposition cycles. FIG. 12 shows how the WGM spectra of a single microsphere shift towards higher wavelengths when multiple layers of PE are deposited on its surface. A similar behavior can be seen for clusters, e.g. for a cluster of 3 microspheres (FIG. 13). The PE layers were adsorbed from aqueous solutions (PAH: 1.5 mg/ml in 0.5 M NaCl aqueous solution, PSS: 1 mg/ml in 0.5 M NaCl solution) and incubated for about 10 min.

Figure 14:
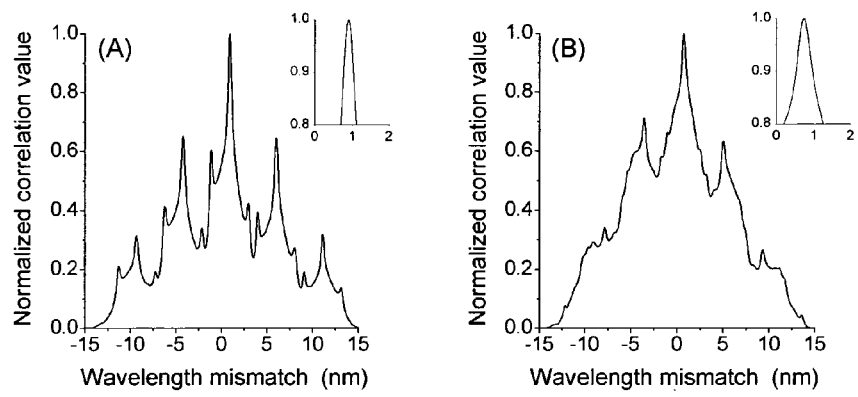
Figure 15:
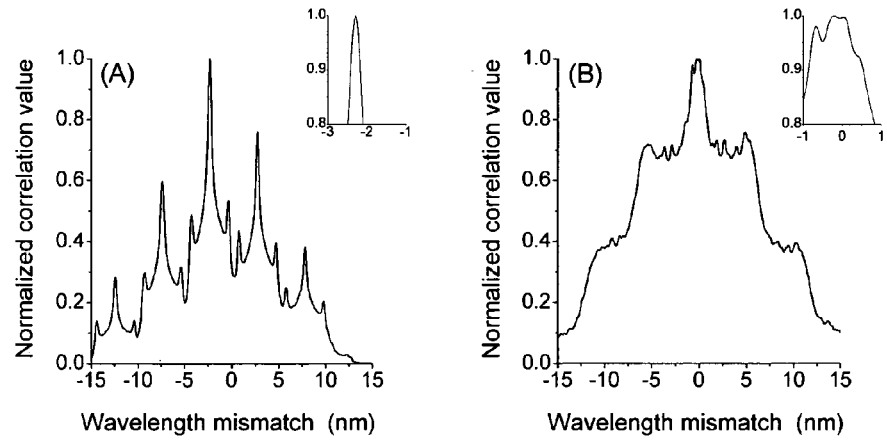

An autocorrelation function was used for data analysis. FIGS. 14A and 14B show the results of the autocorrelation of spectra prior to the adsorption of PE with those obtained after the third coating for a single microsphere (cf. FIG. 12) and a cluster of 3 microspheres (cf. FIG. 13), respectively. In both graphs, a pronounced maximum with a high correlation value and narrow width can be seen. From the position of this maximum, the average wavelength shift of the WGM due to adsorption of the PE layers can be directly determined. To verify that the autocorrelation function can also be used to distinguish different clusters from each other, similar calculations have been performed between different clusters as well as different single microspheres as displayed in FIG. 15. For different single microspheres the correlation yields a similar result as obtained when calculating the correlation between two different spectra from the same sphere (FIG. 15A), which confirms that single microspheres cannot be identified by this method. In particular the correlation maximum is as symmetric and narrow as that of FIG. 14A. However, when the correlation is calculated between WGM spectra obtained from different clusters (FIG. 15B), the lineshape of the correlation maximum is significantly broadened and is no longer symmetrical, which means that such correlation can be clearly distinguished from the case of correlating different spectra of the same cluster (cf. FIG. 14B). Thus, the unique lineshape of the WGM spectra of clusters is confirmed and can be used for their identification, e.g. by the method described here.

Figure 16:
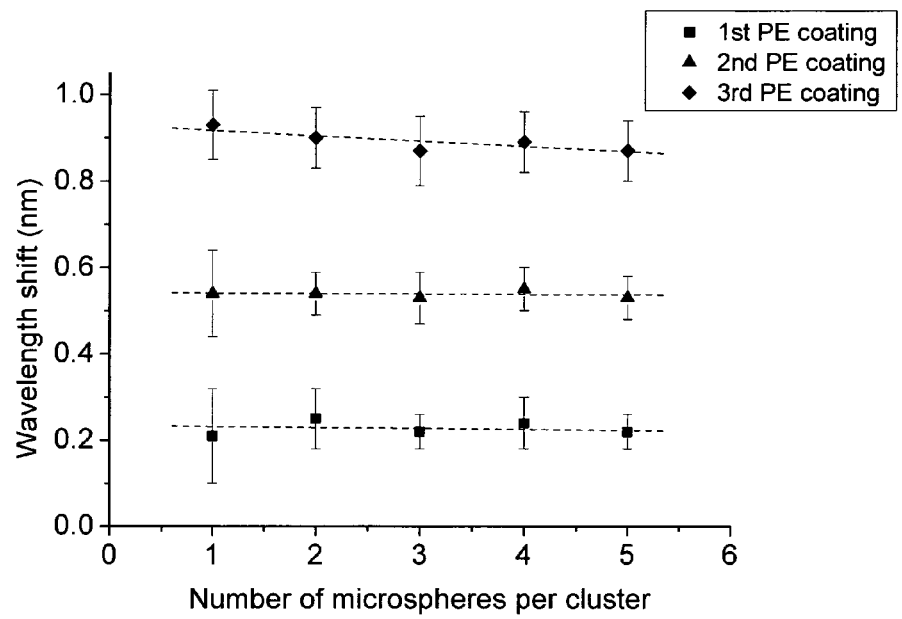
FIG. 16 displays the average WGM wavelength shift due to subsequent PE deposition as a function of the number of beads present in the cluster for 1 to 3 PE layers; the error bars indicate the experimental errors calculated from averaging over 5-6 measurements on different clusters of same bead number.

FIG. 16 shows the average WGM wavelength shift of different clusters of microspheres for various deposition thicknesses of PE. It can be seen that the WGM wavelength shift does not depend on the number of beads present in the cluster but only on the thickness of the deposited PE and further is identical within the error to the shift observed for a single microsphere. Thus, the number of microresonators in a cluster needs not to be precisely controlled. Further, for the calculation of general properties, such as the average thickness (or density) of the adsorbed layer, the theory for single spheres can be applied. Due to the excellent agreement between clusters and single spheres, the average WGM shifts obtained for single spheres and clusters of different size will be used for the following determination of the adsorbate layer thickness as a function of the number of deposited PE layers.

Assuming that the difference in the refractive index between PS sphere and PE is small, the thickness of the PE coating can be calculated from the WGM wavelength shift according to the following equation.

$$\frac{\partial \omega}{\omega} = -\frac{n_L}{n_S} \frac{\partial R}{R} \quad (5)$$

Here, $\partial \omega$ is the frequency shift of the WGM under consideration, $\omega$ is its initial frequency, $\partial R$ the increase of the microsphere radius due to the adsorbate, R the initial microsphere radius, and $n_L$ and $n_S$ are the refractive indices of deposited layer and microsphere, respectively.

Table 1 shows a comparison of the thickness of the PE coatings as experimentally determined by means of the WGM shifts with their corresponding values according to reference data obtained via neutron reflectometry (M. Losche et al., Macromolecules 31, pp. 8893-8906, 1998) and light scattering experiments (Caruso et al., Science, 282, pp. 1111-1114, 1998). It can be seen that except for the first coating, where the thickness measured with the WGM sensor is slightly below the expected value, the results match the literature values very nicely.

TABLE 1

| Number of polyelectrolyte coatings | Δλ (nm) | Measured thickness (nm) | Reference thickness (nm) |
|---|---|---|---|
| 1 | 0.23 | 2.5 | 3 |
| 2 | 0.54 | 5.8 | 6 |
| 3 | 0.89 | 9.5 | 9 |

Altogether, our findings demonstrate that clusters of microspheres can be used as optical (bio-)sensors in the same way as single microspheres. Clusters exhibit the same WGM shift when a molecule is adsorbed on their surface compared to a single microsphere. Moreover, the WGM wavelength shift does not depend on the number of microspheres present in the cluster. It has also been demonstrated that each cluster exhibits a particular WGM spectrum that can be considered as its fingerprint. This feature is particularly interesting for arrays of sensors, because each cluster can be identified by the characteristic lineshape of its WGM spectrum, even when the spectrum is shifted due to adsorption of analyte. This surprising finding supersedes any tedious recording of the exact position of the clusters, and therefore drastically simplifies the detection scheme. In combination with the autocorrelation function described above, cluster identification and evaluation of the observed peak shift can be performed in a single step.

Example 2

Adsorption Bovine Serum Albumin on Single Beads and Clusters of Beads

The main application of a biosensor is obviously to detect whether wanted biomolecules are present in the analyte. Consequently, an attempt to detect the presence of a protein in solution and to characterize the performance of the biosensor in view of its sensitivity limit was carried out. The protein chosen for this test is Bovine Serum Albumin (BSA), because it is a well-known protein that is commonly used for passivation.

The biosensor itself consists of clusters of polystyrene microspheres (r=5 μm), doped with a laser dye (C6G) in order to produce WGM under external excitation (CW HeCd laser operated at 442 nm), such as described above. The microspheres are randomly deposited on a glass cover slip, and a flow cell is built around the microspheres in order to perform the measurements in situ.

Figure 17:
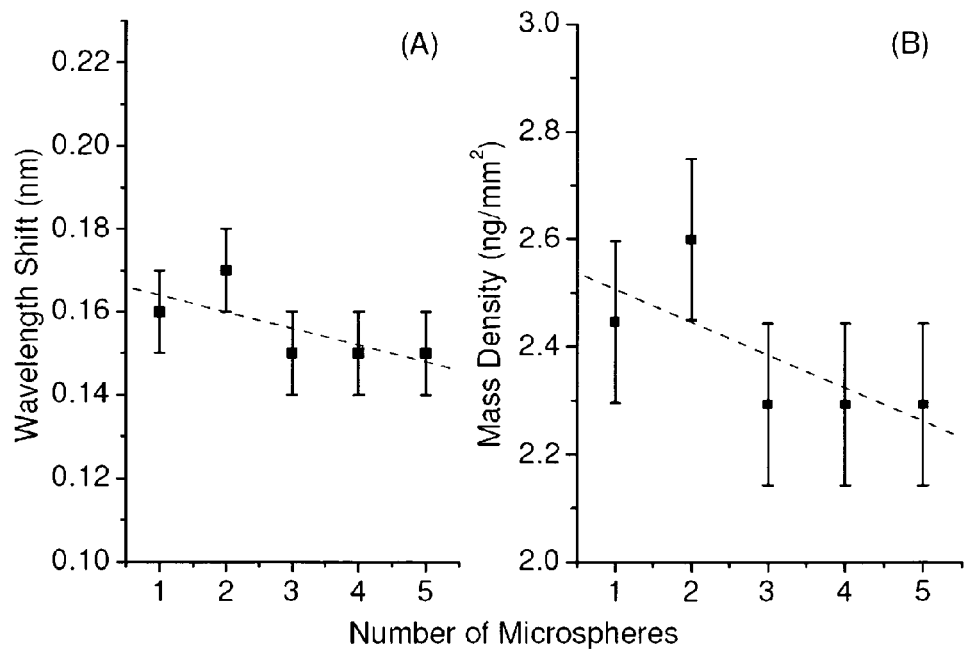

First, the WGM spectra of clusters of various sizes are measured in PBS buffer prior to any deposition of BSA. Then, 0.1% BSA solution (in standard PBS buffer, pH 7.4) is let into the flow cell and, after an incubation time of about 15 minutes, another series of WGM spectra of the same clusters is acquired. FIG. 17 represents the mean wavelength shift of the traced WGM after injection of the BSA solution into the flow cell for about 1 hour and subsequent rinsing with PBS buffer as a function of the number of microspheres forming the clusters. As already found in the first example, single microspheres and clusters of microspheres exhibit the same WGM wavelength shift upon adsorption of the BSA. The small deviations that can be observed (FIG. 17A) are still within the experimental errors (as calculated as standard deviations over five independent experiments) and also below the resolution limit of the detection setup used (down to 0.01 nm). Thus, the theory derived for single spheres commonly used in order to calculate various parameters, such as the projected area of the BSA molecule on the sphere surface, can also be used in the case of clusters of microspheres. In the following calculations, it is assumed that a full monolayer of BSA molecules has formed on the clusters' surface. The projected area ($\sigma_P^{-1}$) of the BSA molecule is calculated from the WGM wavelength shift of the TE modes using the following equations.

$$\frac{\partial \omega}{\omega} = -\frac{n_L}{n_S}\frac{\partial R}{R} \quad (5)$$

$$\sigma_P = \frac{\partial R \varepsilon_0 (n_s^2 - n_m^2)}{\alpha_{ex}} \quad (6)$$

Here, $n_s$, $n_m$ and $n_L$ are the refractive indices of bead (1.59), the surrounding medium (1.33) and BSA (1.5), respectively. $\alpha_{ex}$ is the excess polarizability of BSA ($4\pi\varepsilon_0 \times 3.85 \times 10^{-21}$ cm$^3$). The calculated projected area ($\sigma_P^{-1}$) varies between $3.98 \times 10^{-13}$ cm$^2$ and $4.51 \times 10^{-13}$ cm$^2$. These values are in good agreement to what has been published about the projected area of BSA, $3.4 \times 10^{-13}$ cm$^2$, by Arnold et al. (Optics Letters, 28, 4, p. 272-274, 2003) and $3.5 \times 10^{-13}$ cm$^2$ by Ferrer et al. (Biophysical Journal, 80, p. 2422-2430, 2001), thus corroborating the assumption of monolayer formation. The current mass sensitivity of our sensor is 1 pg considering a microsphere (r=5 μm) covered with a full monolayer of BSA molecules (M=66000 g/mol). The absolute mass sensitivity limit is about 100 fg, assuming that a WGM wavelength shift of about 10% that of the shift induced by adsorption of a full monolayer of BSA can be measured. With the current sphere size, this corresponds to a minimum detectable wavelength shift of 0.01 nm, which is easily possible with the optical setup used in the experiments.

Comparative Example 1

Vollmer et al. (Applied Physics Letters, 80, 21, p. 4057-4059, 2002) have performed similar experiments regarding the adsorption of BSA on microspheres for biosensing. In their case, the WGM sensor consists of a single microsphere made from silica with a diameter of 300 μm. The microsphere was fabricated by melting the tip of an optical fiber with a butane/nitrous oxide microflame torch. Both the excitation and the detection of the WGM are achieved via an optical fiber. The positioning of the optical fiber with respect to the microsphere has to be very precise, since WGM excitation requires a nanometer scale gap between the optical fiber and the microsphere. The changes of the WGM positions due to biomolecular adsorption are detected by tracing the intensity changes in the optical field transmitted through the optical fiber. The scanning of the excitation wavelength is performed by an accordable DFB laser with a precision of 0.009 nm/mA. The adsorption of a full monolayer of BSA on the biosensor surface caused a WGM wavelength shift of 0.021 nm.

Compared to the sensor fabricated by Vollmer et al., the sensor presented here is more sensitive in terms of the absolute mass of biomolecules adsorbed on the sensor surface required to form a full monolayer. Moreover, the WGM wavelength shift is larger ($\Delta\lambda_{WGM}$=0.2 nm). These features are due to the smaller size of the microspheres used to build the sensor. An additional advantage is that the excitation and detection schemes are simplified and do not require any coupling with an optical fiber because of the incorporation of the fluorescent material into the microresonators. Besides the potential for remote sensing, this further enables the utilization of clusters of microresonators as biosensor instead of single microspheres, which greatly improves the feasibility of the detection scheme as described above.

Example 3

Clusters of Microresonators Operated in the Stimulated Emission Regime

In the examples above, the fluorescent microresonators were excited by means of cw laser radiation at low to moderate pump intensity. In the following, we will describe the impact of pumping the microresonators by means of a pulsed laser above the threshold for stimulated emission, i.e. the lasing threshold.

Experimental.

PS beads with a nominal diameter of 15 μm (Polysciences, Inc., Warrington, Pa., USA) were doped with Nile red using a method known to those skilled in the art. Subsequently, the suspension was first diluted with Millipore water to reduce the number of beads (typically 50-100 fold), then a small drop (10-20 μl) of suspension was dropped onto a glass cover slip bearing a viton sealing. The water level was raised to the top of the sealing by additional Millipore water, then the system was sealed by means of a quartz substrate as top cover. That way, the samples were not allow to dry, and the beads sank to the substrate only due to gravitational forces, thereby remaining in weak van-der-Waals interaction with the substrate, i.e. they were almost freely floating and only stationary due to lack of (convective) flows in the liquid cell. The microresonators and clusters thereof were excited by means of the 2$^{nd}$ harmonic of a Nd:YAG picosecond laser with variable repetition rate (10-500 kHz) and a pulse duration of 9 ps. The laser emission was coupled into the inverted microscope via a built-in fluorescence filter block, such that microresonator excitation and detection were mediated through the same microscope objective (Nikon 100×). The pulse energy could be either varied by rotating a lambda half plate in front of the nonlinear optical crystal used for 2$^{nd}$ harmonic generation or simply by varying the repetition rate of the laser pulses, while keeping the average power constant. For detection, the same system was applied as in the examples above (Horiba Jobin Yvon Triax 550 equipped with an Andor cooled CCD camera).

Results.

Figure 20:
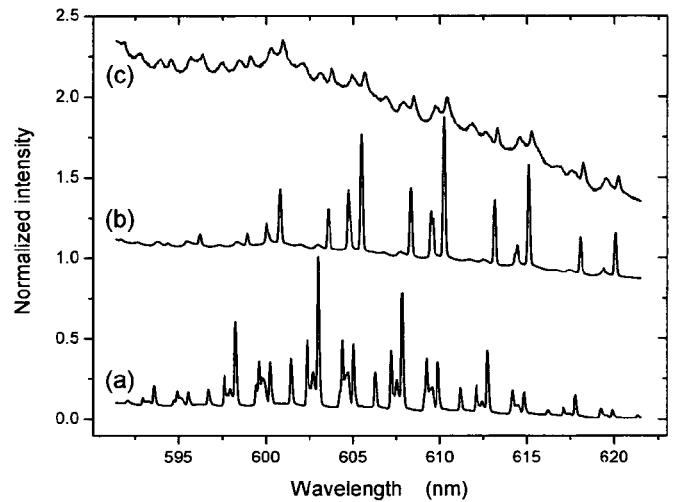
FIG. 20 shows WGM spectra of two different trimers in water, wherein (a) and (b) are spectra from central excitation above the lasing threshold, (c) is a spectrum from central excitation below the lasing threshold, and (b) and (c) are spectra obtained from the same cluster.

FIG. 20 displays WGM spectra obtained from two different trimers of 15 μm PS beads, both forming triangles of basically equal side length (cf. sketch in FIG. 21), excited above and below the lasing threshold. WGM spectrum (c), which was acquired below the lasing threshold, resembles the fingerprint lineshape as found in the examples above. When this trimer is pumped above threshold (spectrum (b)), the lineshape changes drastically, because not all WGM reach the lasing threshold under the same conditions and with same efficiency. Besides a change in the relative intensities, in particular a smaller number of modes is observable in spectrum (b). Nevertheless, comparing the two spectra shows that all modes observable in spectrum (b) can be related to peaks in the WGM spectrum below threshold (c). It should be noted that the "missing" peaks are still present in spectrum (b), however, they are "buried" in the background due to their much lower intensity as compared to the lasing modes (the spectra of FIG. 20 were normalized to their respective maximum intensity to facilitate the comparison of mode positions and general lineshape and normalized to vertically displaced for clarity).

Because of these obvious differences in the lineshape below and above threshold, respectively, the most important question for the present embodiment is whether—despite of the smaller number of modes—the fingerprint characteristics of the spectra may be preserved also in the stimulated emission regime. That this the case, is exemplified by spectrum (a), which was obtained under lasing conditions from the second trimer. Due to the size distribution of the PS beads, the different lasing modes appear at different positions as compared to spectrum (b). Also, the lineshape is different due to the presence of additional modes. This indicates that sensors based on clusters of microresonators may be operated above the lasing threshold without losing their individual—though somewhat altered—fingerprint, while taking advantage of the much better signal-to-noise ratio and the smaller linewidth of the lasing modes (cf. an U.S. provisional patent application No. 61/112,410 which was filed on Nov. 7, 2008). In particular the smaller linewidth further improves the sensitivity of the sensor, because even smaller wavelength shifts may be resolved with narrower modes.

Example 4

Selective Analysis of Microresonators within a Cluster by Selective Lasing

This example further explores the potential of operating microresonators above the lasing threshold. Due to the significant difference in emission intensity between lasing and non-lasing modes, individual microresonators within a cluster can be analyzed in view of their WGM spectra independently, if they can be separately operated above the lasing threshold. In such case, the fingerprint spectrum emerging from other, non-lasing members of the cluster, is simply buried in the background as illustrated in the example above (FIG. 20).

Figure 21:
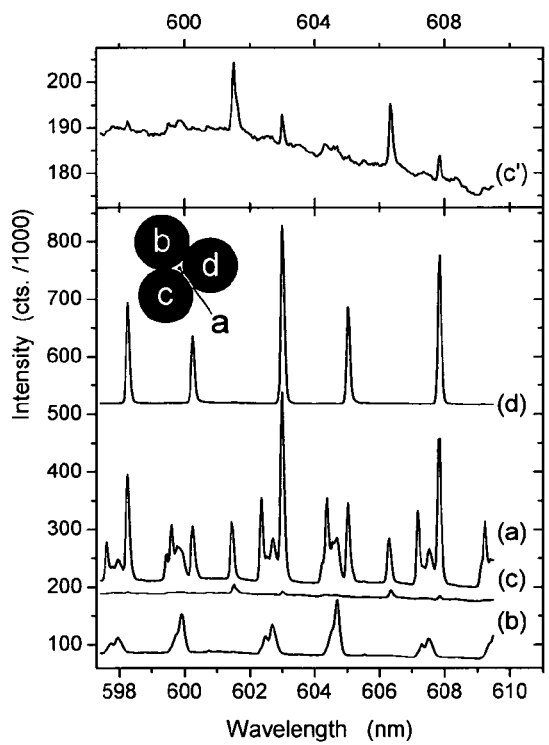
FIG. 21 shows WGM spectra obtained from a trimer immersed in water and excited at different locations as indicated in the sketch of the trimer; wherein (a) central excitation, (b) excitation of upper left bead, (c) excitation of lower left bead, and (d) excitation of right bead (all other parameters, in particular excitation intensity, kept constant)

FIG. 21 exemplifies this procedure (experimental details same as in Example 3). As illustrated by the sketch in the FIG. 21, the trimer was excited in different ways by focusing the laser beam onto different regions. The diameter of the beam focus was about 30 μm and thus about twice the nominal particle diameter, however, with an about four-fold higher intensity in the beam center, which allowed selective pumping of individual microresonators within the trimer above the lasing threshold. Spectrum (a) was acquired by aligning the beam center into the center of the trimer, thus pumping all three beads above threshold. Spectra (b)-(d) were then obtained by aligning the beam center onto the different beads as indicated in the sketch. Spectra (b) and (d) clearly show lasing of the respective beads, while spectrum (c) is below threshold. It should be noted that FIG. 21 shows non-normalized raw data as acquired with the CCD camera (0.1 s acquisition time accumulated over 10 acquisitions) for direct comparison of the different WGM intensities achieved. Because of its low intensity, a blow-up of spectrum (c) is shown in the upper half of FIG. 21 (c'). Spectra (b)-(d) all show the characteristics of WGM obtained from individual beads in water (cf. FIG. 6B) and thus allow for the individual analysis of the selected bead. At the same time, however, the cluster exhibits a characteristic fingerprint spectrum, thereby facilitating its identification. In combination of these two effects, an individual microresonator on surface can be addressed by firstly identifying its host cluster by its characteristic fingerprint spectrum (by excitation above threshold of all (most) members of the cluster), followed by a selective excitation above threshold of the wanted bead only. It should be noted that due to the typically small number of microresonators within one cluster (typically 2-8), the individual microresonators within the cluster may be distinguished by their single particle spectra due to their size variation, which makes it very unlikely to have two particles of identical size (within the resolution of the detection system) out of thousands of particles in suspension within the same cluster. This way of addressing individual microresonators within a cluster may be of interest, for example, when bead radii and/or other parameters, such as the refractive index of the ambient and/or the characteristics of the adsorbate, need to be precisely determined. In such case, the slight differences in the WGM mode shifts due to different microresonator size and different mode polarizations (TE, TM) may be precisely measured and used for a more sophisticated analysis of the measurement. Also, in the case that different microresonators within the same cluster bear different functionalization, e.g. for targeting different (bio-)molecules or bearing a passivation layer for reference purpose, individual read-out of microresonators within a cluster may be wanted. In such case, the basic idea of fingerprint spectra may be maintained for small differences in the wavelength shifts of the individual microresonators comprising the cluster or by the analysis of fingerprint spectra of subsets of microresonators of the cluster. In the latter case, subset spectra may be also numerically overlapped in such way that the overall fingerprint is maintained (e.g. by correcting the wavelength axis according to the individual wavelength shifts measured for the different subsets and subsequent numerical superposition of the corrected subset spectra).

Example 5

Selective Analysis of Microresonators within a Cluster by Applying More than One Fluorescent Material In the above example, selective analysis of microresonators within a cluster was achieved by taking advantage of the significant differences in mode intensity above and below the lasing threshold, respectively. In an alternative scheme, such significant difference in mode intensity may be achieved by utilization of different excitation schemes for the different members of a cluster. In the present examples, which apply dye-doped PS beads, such different excitation scheme may be achieved easily by doping the particles with different fluorescent dyes and by utilization of excitation light sources with suitable excitation wavelengths allowing selective dye excitation. To achieve fingerprint spectra of the whole cluster, however, the emission wavelength range of the different dyes applied should overlap to sufficient extent, i.e. allowing for the acquisition of fingerprint spectra with sufficient details for their distinction from other clusters within the sample.

In the following, a simple example of this technique is given.

Experimental.

To obtain PS beads with different excitation but overlapping emission wavelength regimes, 15 μm PS beads were doped with a mixture of C6G and Nile red. As shown in Examples 1 and 2, C6G can be excited at 442 nm, while Nile red does hardly absorb in this regime. C6G emits in the range from 490-550 nm, which is basically the range of Nile red excitation. Therefore, a bead that contains both dyes, can be excited either at 442 nm via the C6G, the emission of which will excite the Nile red present in the bead, or at 532 nm, where the Nile red is directly pumped. In both cases, the emission wavelength range is from about 580 nm to 650 nm and thus basically matches the emission wavelength range of PS beads solely doped with Nile red.

For particle excitation, the HeCd laser operated at 442 nm and the Nd:YAG picosecond laser operated at 532 nm were applied as in the examples above. Because different optical set-ups were used for beam guidance of the two laser beams (HeCd laser from top of the sample as illustrated in FIG. 5 and Nd:YAG laser through the microscope objective), the clusters could be effortlessly exposed to both beams simultaneously and/or to one of the beams only.

The samples (clusters of PS beads) were prepared by dispersing a mixture of 15 µm PS beads in water, some of which doped with C6G and Nile red, some of which doped with Nile red only, onto a cleaned microscope cover slip. Clusters were selected for analysis by verifying that only some beads within a cluster could be effectively excited by means of the 442 nm radiation, while others could be not. Such a "mixed" cluster will be studied in the following.

Results.

Figure 22:
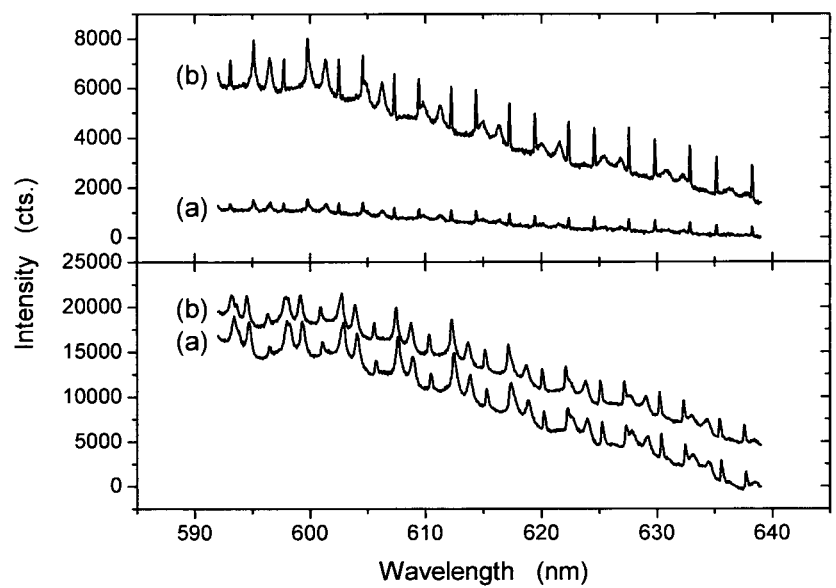
FIG. 22 shows WGM spectra of 15 µm PS beads, which were either doped with Nile red only (upper half) or doped with C6G and Nile red (lower half), and were excited either by 442 nm radiation (a) or by 532 nm radiation (b), respectively.

In a first step it was verified that the two kinds of beads used (doped with Nile red only: "Type I"; doped with C6G AND Nile red: "Type II") in fact achieved different emission intensity in the overlapping emission wavelength regime. This was verified by exposing single microresonators of the two kinds to the two different excitation sources. FIG. 22 displays typical results. In the upper half a single PS bead of Type I is exposed to the 442 nm radiation (a) and to the 532 nm radiation (b), respectively. Obviously, the 532 nm radiation is much more effective in exciting WGM. It should be noted that the spectra of FIG. 22 show non-normalized raw data as obtained from the CCD camera for direct comparison of their WGM intensities (spectra (b) were slightly displaced for clarity). Also, the laser intensities were set such that they achieved WGM spectra of similar strength. Because the HeCd laser is a cw laser of moderate output power, lasing could not be achieved. Therefore, also the picosecond Nd:YAG laser was operated below threshold.

In the lower half of FIG. 22, the spectra obtained from a Type II bead are shown for excitation with the 442 nm radiation (a) and the 532 nm radiation (b), respectively. Because of the presence of C6G in this bead, the Nile red can be effectively excited through the C6G emission, so that the WGM spectra obtained from the bead are basically independent of the source of excitation.

Accordingly, fingerprint spectra of clusters may be obtained by excitation of the cluster at 532 nm, where all beads utilized can be effectively excited, while individual beads (Type II only) can be addressed by using the 442 nm radiation.

Figure 23:
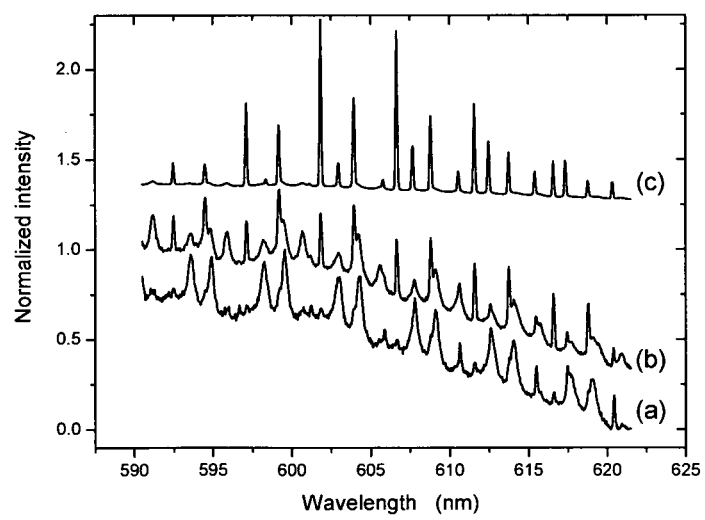
FIG. 23 shows normalized WGM spectra of a mixed dimer comprised of one bead doped with Nile red only and one bead doped with C6G and Nile red, wherein (a) the dimer was centrally excited by 442 nm radiation, (b) the dimer was centrally excited by 532 nm radiation below the lasing threshold, and (c) the dimer was centrally excited by 532 nm radiation above the lasing threshold.

As a demonstration of this principle, FIG. 23 shows normalized spectra obtained from a mixed dimer (one bead of Type I and one bead of Type II) excited with the 442 nm radiation (a) and the 532 nm radiation (b), respectively. In spectrum (a), despite of some minor contributions from other modes (possibly originating from the Type I bead), the first order TM/TE pairs characteristic for single beads in aqueous environment (cf. FIG. 6B and, e.g., P. Ziglstra et al., Appl. Phys. Lett. Vol. 90, pp. 161101/1-3, 2007; S. Pang et al. Appl. Phys. Lett. Vol. 92, pp. 221108/1-3, 2008;) can be clearly identified and thus used for analysis of the Type II bead. Information about the Type I bead may then be obtained for example by subtracting spectrum (a) from spectrum (b). Here, however, we make use of the different emission characteristics of the excitation lasers for accessing information about the Type I bead. As shown in spectrum (c), the pump intensity of the 532 nm radiation was raised above the lasing threshold, thus yielding a lasing spectrum of the Type I bead only (cf. Examples 3 and 4). Again, the spectrum exhibits the characteristic TM/TE pairing, this time however showing the WGM of the Type I bead solely (all other non-lasing modes buried in the background as discussed in the examples above). The reason why only the Type I bead is lasing is related to the observation that in the batch of particles used, the C6G/Nile red doped beads exhibited a somewhat broader bandwidth and accordingly lower Q-factor than the beads doped with Nile red only (cf. FIG. 22). While the reason for this difference is presently unclear, it may be used for selective lasing of the Type I bead, because in general, modes with the highest Q-factors show the lowest lasing thresholds. Therefore, by proper choice of the pump intensity, lasing of only the Type I bead could be achieved.

The latter procedure shows that the different schemes for selective excitation (use of different fluorescent dyes and lasing, respectively) may be also combined to yield information about individual microresonators within a cluster and that individual spectra may be obtained below and above the lasing threshold, depending on the scheme utilized for their excitation.

The applications for the procedures presented in this example are basically the same as discussed at the end of Example 4, i.e. are related to an improved analysis and to the application of differently functionalized microresonators within a cluster.

The invention claimed is:

1. A method for sensing a target object using optical mode excitations in microresonators, comprising:
preparing at least one cluster including at least two microresonators;
obtaining at least one first spectrum of the cluster;
adsorbing the target object on a surface of the cluster;
obtaining at least one second spectrum of the cluster; and
sensing the target object by comparing a lineshape of the at least one first spectrum with a lineshape of the at least one second spectrum, wherein
the at least one first spectrum is collectively obtained from the microresonators included in the cluster, and
the at least one second spectrum is collectively obtained from the microresonators included in the cluster.

2. The method according to claim 1, wherein
the cluster is deposited on a substrate.

3. The method according to claim 1, wherein
the cluster is floated in a fluidic cell.

4. The method according to claim 1, wherein
the type of a part of the microresonators in the cluster is different from the type of the other part of the microresonators in that cluster.

5. The method according to claim 1, wherein
the at least one first spectrum of the cluster is obtained after introduction of a probe molecule to adsorb the target object on the surface of the cluster and passivation of non-specific binding sites on the surface of the cluster.

6. The method according to claim 1, wherein
the target object is adsorbed on the surface of the cluster by exposing the cluster to an analyte containing the target object.

7. The method according to claim 1, wherein
the target object is detected by determining a magnitude of a wavelength shift between the lineshape of the at least one first spectrum and the lineshape of the at least one second spectrum in at least a part of the measured range.

8. The method according to claim 1, wherein
the at least one second spectrum corresponding to the at least one first spectrum is identified and an average peak shift between the lineshape of the at least one first spectrum and the lineshape of the at least one second spectrum is obtained based on an autocorrelation between the lineshape of the at least one first spectrum and the lineshape of the at least one second spectrum.

9. The method according to claim 1, preparing a plurality of clusters;

obtaining the at least one first spectrum of each of the clusters;

adsorbing the target object on the surface of at least a part of the clusters;

obtaining the at least one second spectrum of each of the clusters; and sensing the target object by comparing the lineshape of the at least one first spectrum prior to the change with the lineshape of the at least one second spectrum after the change.

10. The method according to claim 9, wherein the shape of a part of the clusters is different from the shape of the other part of the clusters.

11. The method according to claim 9, wherein the type of a part of the microresonators in at least one of the clusters is different from the type of the other part of the microresonators in that cluster.

12. The method according to claim 9, wherein a part of the clusters is separated from the other clusters.

13. The method according to claim 9, wherein a part of the clusters is functionalized in a different way from the other part of the clusters.

14. The method according to claim 9, wherein the at least one first spectrum and the at least one second spectrum are obtained by recording an image scan of the surface of the clusters at once or in a sequence of measurements.

15. A biosensor chip for sensing a target object using optical mode excitations in microresonators, comprising:

a substrate having a surface; and at least one cluster including at least two microresonators disposed on the surface of the substrate, wherein, all microparticles within the cluster are operated collectively.

16. The biosensor chip according to claim 15, wherein, a plurality of the clusters are disposed on the surface of the substrate, whereby, if a cluster out of this plurality is operated, all microparticles within that cluster are operated collectively.

17. The biosensor chip according to claim 15, wherein, the shape of a part of the clusters is different from the shape of the other part of the clusters.

18. The biosensor chip according to claim 15, wherein, the type of a part of the microresonators in at least one of the clusters is different from the type of the other part of the microresonators in that cluster, whereby all microparticles within the cluster are operated simultaneously.

19. The biosensor chip according to claim 16, wherein, a part of the clusters is separated from the other clusters.

20. The biosensor chip according to claim 16, wherein, a part of the clusters is functionalized in a different way to the other part of the clusters.

* * * * *